(12) United States Patent
Wang et al.

(10) Patent No.: US 10,258,666 B2
(45) Date of Patent: Apr. 16, 2019

(54) INHIBITORS OF PHOSPHATASE AND TENSIN HOMOLOG (PTEN) COMPOSITIONS, USES AND METHODS

(71) Applicant: THE UNIVERSITY OF BRITISH COLUMBIA, Vancouver (CA)

(72) Inventors: Yu Tian Wang, Vancouver (CA); Shu Zhang, Vancouver (CA); Changiz Taghibiglou, Saskatoon (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 14/810,223

(22) Filed: Jul. 27, 2015

(65) Prior Publication Data

US 2016/0074472 A1  Mar. 17, 2016

Related U.S. Application Data

(62) Division of application No. 13/501,645, filed as application No. PCT/CA2010/001656 on Oct. 15, 2010, now Pat. No. 9,127,079.

(60) Provisional application No. 61/272,655, filed on Oct. 16, 2009.

(51) Int. Cl.
| | |
|---|---|
| *A61K 38/17* | (2006.01) |
| *A61K 9/00* | (2006.01) |
| *C07K 14/47* | (2006.01) |
| *A61K 39/395* | (2006.01) |
| *A61K 47/64* | (2017.01) |
| *A61K 38/00* | (2006.01) |

(52) U.S. Cl.
CPC ........ *A61K 38/1709* (2013.01); *A61K 9/0019* (2013.01); *A61K 39/3955* (2013.01); *A61K 47/645* (2017.08); *C07K 14/4702* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,960,790 A | 10/1990 | Stella et al. | |
| 5,087,616 A | 2/1992 | Myers et al. | |
| 5,420,105 A | 5/1995 | Gustavson et al. | |
| 6,127,349 A | 10/2000 | Chasalow | |
| 6,204,054 B1 | 3/2001 | Sutton et al. | |
| 6,214,966 B1 | 4/2001 | Harris | |
| 6,380,253 B1 | 4/2002 | Das | |
| 6,482,795 B1 | 11/2002 | Steck et al. | |
| 7,067,494 B2 | 6/2006 | Anderson et al. | |
| 7,744,879 B2 | 6/2010 | Shusta et al. | |
| 2006/0154963 A1 | 7/2006 | Hong | |

FOREIGN PATENT DOCUMENTS

| | | |
|---|---|---|
| WO | WO 1999002704 | 1/1999 |
| WO | WO 2009117387 | 9/2009 |

OTHER PUBLICATIONS

Sung et al., Biochimica et Biophysica Acta 1758 pp. 355-363.*
Ballard et al. (1998) "Anthrax toxin-mediated delivery in vivo and in vitro of a cytotoxic T-lymphocyte epitope from ovalbumin" *Infect. Immun* 66(2):615-619.
Blanke et al. (1996) "Fused polycationic peptide mediates delivery of diphtheria toxin A chain to the cytosol in the presence of anthrax protective antigen" *Proc Natl Acad Sci USA* 93(16):8437-8442.
Bork (2000) "Powers and Pitfalls in Sequence Analysis: The 70% Hurdle" *Genome Research* 10:398-400.
Bowie et al. (1990) "Deciphering the message in protein sequences: tolerance to amino acid substitutions" *Science* 247(4948):1306-1310.
Brownell et al. (1998) "In vivo PET imaging in rat of dopamine terminals reveals functional neural transplants" *Ann Neurol* 43(3):387-390.
Carmichael et al. (2004) "Evolution of diaschisis in a focal stroke model" *Stroke* 35(3):758-763.
Demarchi et al. (1996) "Activation of transcription factor NF-kappaB by the Tat protein of human immunodeficiency virus type 1" *J Virol* 70(7):4427-4437.
Dilber et al. (1999) "Intercellular delivery of thymidine kinase prodrug activating enzyme by the herpes simplex virus protein, VP22" *Gene Ther.* 6(1):12-21.
Fujihara & Nadler (1999) "Intranuclear targeted delivery of functional NF-kappaB by 70 kDa heat shock protein" *EMBO J* 18(2):411-419.
Gregorian et al. (2009) "Pten deletion in adult neural stem/progenitor cells enhances constitutive neurogenesis" *J Neurosci* 29(6):1874-1886.
Hamacher et al. (1986) "Efficient stereospecific synthesis of no-carrier-added 2-[18F]-fluoro-2-deoxy-D-glucose using aminopolyether supported nucleophilic substitution" *J. Nucl. Med.* 27(2):235-238.
Hariton-Gazal et al. (2002) "Targeting of nonkaryophilic cell-permeable peptides into the nuclei of intact cells by covalently attached nuclear localization signals" *Biochemistry* 41(29):9208-9214.
Kornblum et al. (2000) "In vivo imaging of neuronal activation and plasticity in the rat brain by high resolution positron emission tomography (microPET)" *Nature Biotechnol* 18(6):655-660.
Li et al. (1997). "PTEN, a putative protein tyrosine phosphatise gene mutated in human brain, breast, and prostate cancer." *Science* 275 (5308): 1943-1947.
Li et al. (2008) "Tat-3L4F does not significantly affect spatial learning and memory" *Behav Brain Res* 193(2):170-173.

(Continued)

*Primary Examiner* — Robert A Zeman
(74) *Attorney, Agent, or Firm* — Carol L. Francis; Bozicevic, Field & Francis LLP

(57) ABSTRACT

Described herein are isolated polypeptides having phosphatase and tensin homolog (PTEN) inhibitory activity, vectors and cells for the expression thereof and methods for their use in treating diseases associated with cytotoxic stress, such as spinal cord injury, stroke, traumatic brain injury, multiple sclerosis, Alzheimer's disease, amyotrophic lateral sclerosis (ALS), Parkinson's disease, and Huntington's disease.

3 Claims, 7 Drawing Sheets
Specification includes a Sequence Listing.

(56) References Cited

OTHER PUBLICATIONS

Li et al. (2009) "Involvement of the PTEN-AKT-FOXO3a pathway in neuronal apoptosis in developing rat brain after hypoxia-ischemia" *J Cereb Blood Flow Metab* 29(12): 1903-1913.
Lian & Di Cristofano (2005) "Class reunion: PTEN joins the nuclear crew" *Oncogene* 24(50):7394-7400.
Morris et al. (2001) "A peptide carrier for the delivery of biologically active proteins into mammalian cells" *Nature Biotechnol* 19(12):1173-1176.
NCBI Reference Sequence: NM_000314.4 "*Homo sapiens* phosphatase and tensin homolog (PTEN), mRNA" Entrez Gene ID: 5728 Jul. 2008.
Ning et al. (2004) "Dual neuroprotective signaling mediated by downregulating two distinct phosphatase activities of PTEN" *J Neurosci* 24(16):4052-60.
Perez et al. (1992) "Antennapedia homeobox as a signal for the cellular internalization and nuclear addressing of a small exogenous peptide" *J Cell Sci* 102(Pt. 4):717-722.
Pooga et al. (1998) "Cell penetration by transportan" *FASEB J* 12(1):67-77.
Prior et al. (1992) "Translocation mediated by domain II of Pseudomonas exotoxin A: transport of barnase into the cytosol" *Biochemistry* 31(14):3555-3559.
Ryser & Shen (1980) "Conjugation of methotrexate to poly (L-lysine) as a potential way to overcome drug resistance" *Cancer* 45(5 Suppl):1207-1211.
Shen & Ryser (1978) "Conjugation of poly-L-lysine to albumin and horseradish peroxidase: a novel method of enhancing the cellular uptake of proteins" *Proc Natl Acad Sci* 75(4):1872-1876.
Shen et al. (2007) "Essential role for nuclear PTEN in maintaining chromosomal integrity" *Cell* 128(1):157-170.
Shyu et al. (2004) "Functional recovery of stroke rats induced by granulocyte colony-stimulating factor-stimulated stem cells" *Circulation* 110(13):1847-1854.
Shyu et al. (2005) "Overexpression of PrPC by adenovirus-mediated gene targeting reduces ischemic injury in a stroke rat model" *J Neurosci* 25(39):8967-8977.
Shyu et al. (2008) "Secretoneurin promotes neuroprotection and neuronal plasticity via the Jak2/Stat3 pathway in murine models of stroke" *J. Clin. Invest* 118(1):133-148.
Steck et al. (1997) "Identification of a candidate tumour suppressor gene, MMAC1, at chromosome 10q23.3 that is mutated in multiple advanced cancers" *Nat. Genet.* 15(4):356-362.
Stenmark et al. (1991) "Peptides fused to the amino-terminal end of diphtheria toxin are translocated to the cytosol" *J Cell Biol* 113(5):1025-1032.
Trotman et al. (2007) "Ubiquitination regulates PTEN nuclear import and tumor suppression" *Cell* 128(1):141-156.
Uniprot KB/Swiss-Prot P60484.1 "RecName: Full=Phosphatidylinositol 3,4,5-trisphosphate 3-phosphatase and dual-specificity protein phosphatase PTEN; AltName: Full=Mutated in multiple advanced cancers 1; AltName: Full=Phosphatase and tensin homolog" Feb. 16, 2004.
Wang et al. (2007) "NEDD4-1 is a proto-oncogenic ubiquitin ligase for PTEN" *Cell* 128(1):129-139.
Wang et al. (2008) "Crucial role of the C-terminus of PTEN in antagonizing NEDD4-1 mediated PTEN ubiquitination and degradation" *Biochem J* 414(2):221-229.
Wiedlocha et al. (1994) "Dual mode of signal transduction by externally added acidic fibroblast growth factor" *Cell* 76(6):1039-1051.
Wolfert & Seymour (1996) "Atomic force microscopic analysis of the influence of the molecular weight of poly(L)lysine on the size of polyelectrolyte complexes formed with DNA" *Gene Ther.* 3(3):269-273.
Zhang et al. Poster "PTEN nuclear translocation induced by NMDAR activation enhances neuronal death" Society of Neuroscience conference, Washington, D.C., Nov. 12, 2011.
Lee, et al. "Pharmacokinetics and Delivery of Tat and Tat-Protein Conjugates to Tissues in Vivo", Bioconjugate Chem. 2001, 12, 995-999.

* cited by examiner a b

A  Female (P = 0.013)

| Statistic | Observed value | Critical value | p-value | alpha |
|---|---|---|---|---|
| Log-rank | 12.616 | 9.488 | 0.013 | 0.050 |

——— K13   ----- K13$_{K-R}$   ▬▬▬ Saline

B  Male (P = 0.342)

| Statistic | Observed value | Critical value | p-value | alpha |
|---|---|---|---|---|
| Log-rank | 4.501 | 9.488 | 0.342 | 0.050 |

——— K13   ----- K13$_{K-R}$   ▬▬▬ Saline

INHIBITORS OF PHOSPHATASE AND TENSIN HOMOLOG (PTEN) COMPOSITIONS, USES AND METHODS

CROSS-REFERENCE TO RELATED APPLICATION

This application claims priority to U.S. Provisional Application No. 61/272,655, filed 16 Oct. 2009.

TECHNICAL FIELD

This invention relates to therapeutics, their uses and methods for the treatment of various indications associated with cytotoxic or excitotoxic stress. In particular, peptides and compositions thereof, having phosphatase and tensin homolog (PTEN) inhibitory activity for use in and methods for the treatment indications associated with cytotoxic or excitotoxic stress.

BACKGROUND

Phosphatase and tensin homolog (PTEN) is a tumor-suppressor reported to be involved in the progression of numerous cancer types (Li et al. 1997; Steck et al. 1997; Baker 2007). PTEN is a negative regulator of the phosphatidylinositol-3-kinase (PI3K)/AKT pathway—loss of PTEN leads to activation of the PI3KJAKT signal cascade and leads to increased cellular growth and proliferation. PTEN has also been shown to have other functions unrelated to PI3K/AKT signaling—for instance, in the maintenance of chromosomal stability through the physical interaction with centromeres and control of DNA repair (Shen et al. 2007). PTEN has been implicated in non-cancer indications, such as stroke, wherein down-regulation of PTEN with siRNA has been shown to have a neuroprotective effect against ischemic neuronal injury in transfected neurons (Ning et al. 2004).

Localization and degradation of PTEN has been shown to involve post-translational modifications, in particular ubiquitination (Trotman et al. 2007; Wang et al. 2007; Wang et al. 2008). PTEN localizes primarily to the cytoplasm, but a distinct pool of PTEN is known to localize to the nucleus (reviewed in (Lian and Di Cristofano 2005)). While PTEN does not contain a canonical nuclear localization signal, it does contain two PEST domains which are frequently found in proteins targeted for degradation by ubiquitination. In fact, polyubiquitination has been shown to target PTEN primarily for cellular degradation (Wang et al. 2007), while monoubiquitination is primarily involved in PTEN nuclear translocation (Trotman et al. 2007). Two specific ubiquitination sites in the PTEN protein sequence, K13 and K289, have been shown to be directly involved in PTEN nuclear translocation—monoubiquitination of either of these sites was shown to be sufficient for nuclear translocation. Mutation of either of these two sites significantly inhibited the nuclear translocation of PTEN (Trotman et al. 2007).

It is unclear whether nuclear translocation occurs in the central nervous system, and if it does, whether mechanisms for such nuclear translocation of PTEN would be the same as in other cells that have been tested to date.

SUMMARY

The present invention is based, in part, on the surprising discovery that mutation of the K13 ubiquitination site of PTEN in neuronal cells significantly reduces nuclear translocation of PTEN, whereas mutation of the K289 ubiquitination site of PTEN in the same cells did not significantly affect nuclear translocation of PTEN. Furthermore, it was surprising that certain novel peptides designed to interfere with ubiquitination at the K13 ubiquitination site of PTEN: 1) block NMDA-induced PTEN nuclear translocation in neuronal cell cultures; 2) block NMDA-induced excitotoxic neuronal injuries in neuronal cultures; 3) block PTEN nuclear translocation in vivo in rat focal ischemia model; 4) reduce stroke-related infarct areas in vivo in a rat focal ischemia model, when administered post-stroke; 5) improve stroke-related long-term motor behavioural recoveries in vivo in rat focal ischemia model, when administered post-stroke; 6) improve behavioural outcomes in a transgenic animal model of ALS; and 7) promote the survival of iPS-NPC (stem cells) transplantated intracerebrally into the infarction areas after focal cerebral ischemia in the rat; whereas when compared to peptides designed to interfere with ubiquitination at the K289 site of PTEN did not exhibit such properties.

In certain aspects of the invention, there is provided an isolated polypeptide composition having an amino acid composition substantially similar to SEQ ID NO: 1 or SEQ ID NO: 2 or SEQ ID NO:5 or SEQ ID NO:6. Wherein substantially similar is meant to encompass a degree of sequence identity when an equivalent region (i.e. ~14 amino acids) is compared. Furthermore, substantially similar is meant to encompass conservative substitutions and modified amino acids provided that the PTEN inhibitory activity or other activities described herein for PTEN K-13 are maintained.

In accordance with one embodiment, there is provided an isolated polypeptide including SEQ ID NO:1 or a polypeptide comprising an 8-14 amino acid sequence having at least 90% identity to SEQ ID NO:1, or a polypeptide comprising an 8-14 amino acid sequence having at least 90% identity to the corresponding amino acids of SEQ ID NO:1, provided that position 8 of SEQ ID NO:1 is lysine (K), and wherein the polypeptide has phosphatase and tensin homolog (PTEN) inhibitory activity. The isolated polypeptide may further include a delivery and targeting (dat) moiety conjugated to the isolated polypeptide. The dat moiety may be selected from one or more of: ligands; receptors; protein transduction domains (PTD); or antibodies. The dat moiety may be a PTD. The isolated polypeptide may include an amino acid sequence selected from SEQ ID NO: 2, SEQ ID NO: 5 or SEQ ID NO: 6. The dat moiety may be selected from antennapedia homeodomain, the translocation domain of diphtheria toxin, the translocation domain anthrax toxin, the translocation domain pseudomonas exotoxin a, dermaseptin s4, hsv-1 vp22, pep-1, the tat protein transduction domain, poly-l-lysine, and poly-d-lysine. The polypeptide may include SEQ ID NO:2.

In accordance with one embodiment, there is provided an isolated polypeptide including SEQ ID NO:1 or a polypeptide comprising an 8-14 amino acid sequence having at least 90% identity to SEQ ID NO:1, or a polypeptide comprising an 8-14 amino acid sequence having at least 90% identity to the corresponding amino acids of SEQ ID NO:1, provided that position 8 of SEQ ID NO:1 is lysine (K), and wherein the polypeptide protects cells from cytotoxic stress or excitotoxic stress. The isolated polypeptide may further include a delivery and targeting (dat) moiety conjugated to the isolated polypeptide. The dat moiety may be selected from one or more of: ligands; receptors; protein transduction domains (PTD); or antibodies. The dat moiety may be a PTD. The isolated polypeptide may include an amino acid sequence selected from SEQ ID NO: 2, SEQ ID NO: 5 or SEQ ID NO: 6. The dat moiety may be selected from antennapedia homeodomain, the translocation domain of diphtheria toxin, the translocation domain anthrax toxin, the translocation domain pseudomonas exotoxin a, dermaseptin s4, hsv-1 vp22, pep-1, the tat protein transduction domain, poly-l-lysine, and poly-d-lysine. The polypeptide may include SEQ ID NO:2.

In accordance with another embodiment, there is provided an isolated polynucleotide comprised of a nucleotide sequence encoding the polypeptide described herein. The polynucleotide may encode an isolated polypeptide including SEQ ID NO:1 or a polypeptide comprising an 8-14 amino acid sequence having at least 90% identity to SEQ ID NO:1, or a polypeptide comprising an 8-14 amino acid sequence having at least 90% identity to the corresponding amino acids of SEQ ID NO:1, provided that position 8 of SEQ ID NO:1 is lysine (K), and wherein the polypeptide has phosphatase and tensin homolog (PTEN) inhibitory activity.

In accordance with another embodiment, there is provided a composition comprising a polypeptide described herein and a carrier. The polypeptide may include a polypeptide selected from one or more of SEQ ID NO:1; SEQ ID NO:2; SEQ ID NO:5; and SEQ ID NO:6 or an amino acid composition substantially similar thereto. The carrier may be selected from the group: a solid support; a stabilizer; a preservative; and a pharmaceutically acceptable carrier.

In accordance with another embodiment, there is provided an isolated polypeptide described herein, which has been recombinantly produced and isolated from a cell.

In accordance with another embodiment, there is provided a vector comprising an isolated polynucleotide including a nucleotide sequence encoding the polypeptide described herein. The polynucleotide may encode an isolated polypeptide including SEQ ID NO:1 or a polypeptide comprising an 8-14 amino acid sequence having at least 90% identity to SEQ ID NO:1, or a polypeptide comprising an 8-14 amino acid sequence having at least 90% identity to the corresponding amino acids of SEQ ID NO:1, provided that position 8 of SEQ ID NO:1 is lysine (K), and wherein the polypeptide has phosphatase and tensin homolog (PTEN) inhibitory activity.

In accordance with another embodiment, there is provided a cell comprising a polynucleotide described herein or a vector described herein, wherein the nucleotide is operably linked to an expression control sequence.

In accordance with another embodiment, there is provided a method of protecting cells from cytotoxic or excitotoxic stress, the method including delivering a polypeptide; selected from one or more of: SEQ ID NO:1; SEQ ID NO:2; SEQ ID NO:5; and SEQ ID NO: 6; to a cell.

In accordance with another embodiment, there is provided a method of protecting cells from cytotoxic or excitotoxic stress, the method including (a) delivering a vector comprising a polynucleotide encoding a polypeptide described herein; to a cell; and (b) expressing the sequence carried by the vector.

In accordance with another embodiment, there is provided a method of expressing a polypeptide, including: (a) providing an expression vector encoding the polypeptide, wherein the polypeptide is selected from one or more of the following: SEQ ID NO: 1; SEQ ID NO: 2; SEQ ID NO:5; SEQ ID NO: 6; (b) introducing the vector into a cell; and (c) maintaining the cell under conditions permitting expression. The introducing the vector into the cell may be done in vivo. The introducing the vector into the cell may be done ex vivo. The introducing the vector into the cell may be done in vitro.

In accordance with another embodiment, there is provided a method for treating a disease associated with cytotoxic stress including administering a biologically effective amount of a PTEN inhibitor, including an isolated polypeptide of SEQ ID NO:1 or a polypeptide comprising an 14 amino acid sequence having at least 90% identity to SEQ ID NO:1 or a polypeptide comprising an 8-14 amino acid sequence having at least 90% identity to SEQ ID NO:1, or a polypeptide comprising an 8-14 amino acid sequence having at least 90% identity to the corresponding amino acids of SEQ ID NO:1, provided that position 8 of SEQ ID NO:1 is lysine (K), and wherein the polypeptide has phosphatase and tensin homolog (PTEN) inhibitory activity, to a subject in need thereof. The cytotoxic stress may be excitotoxic stress.

In accordance with another embodiment, there is provided a method for enhancing stem cell survival following transplantation of a stem cell, including administering a biologically effective amount of an isolated polypeptide comprising SEQ ID NO:1 or a polypeptide comprising an 14 amino acid sequence having at least 90% identity to SEQ ID NO:1 or a polypeptide comprising an 8-14 amino acid sequence having at least 90% identity to SEQ ID NO:1, or a polypeptide comprising an 8-14 amino acid sequence having at least 90% identity to the corresponding amino acids of SEQ ID NO:1, provided that position 8 of SEQ ID NO:1 is lysine (K), and wherein the polypeptide has phosphatase and tensin homolog (PTEN) inhibitory activity, to a subject in need thereof.

In accordance with another embodiment, there is provided a pharmaceutical composition for treating a disease associated with cytotoxic stress, the pharmaceutical composition including a polypeptide described herein and a pharmaceutically acceptable carrier. The disease associated with cytotoxic stress may be selected from spinal cord injury, stroke, traumatic brain injury, multiple sclerosis, Alzheimer's disease, amyotrophic lateral sclerosis (ALS), Parkinson's disease, and Huntington's disease. The cytotoxic stress may be excitotoxic stress.

In accordance with another embodiment, there is provided a use of a polypeptide described herein for preparation of a medicament for treating a disease associated with cytotoxic stress. The cytotoxic stress may be excitotoxic stress.

In accordance with another embodiment, there is provided a use of a polypeptide of described herein for treating a disease associated with cytotoxic stress.

In accordance with another embodiment, there is provided a use of a pharmaceutical composition including a polypeptide described herein and a pharmaceutically acceptable carrier for treating a disease associated with cytotoxic stress. The cytotoxic stress may be excitotoxic stress.

In accordance with another embodiment, there is provided a commercial package including (a) a polypeptide described; and (b) instructions for the use thereof for treating a disease associated with cytotoxic stress. The cytotoxic stress may be excitotoxic stress.

In accordance with another embodiment, there is provided a commercial package including (a) a polypeptide described herein and a pharmaceutically acceptable carrier; and (b) instructions for the use thereof for treating a disease associated with cytotoxic or excitotoxic stress.

In accordance with another embodiment, there is provided a commercial package including (a) a pharmaceutical composition described herein; and (b) instructions for the use thereof for treating a disease associated with cytotoxic stress. The cytotoxic stress may be excitotoxic stress.

In other embodiments, there is provided a method for preventing, inhibiting or reducing ubiquitination of PTEN in a cell, the method comprising contacting the cell with a polypeptide having an amino acid composition substantially similar to SEQ ID NO: 1 or SEQ ID NO: 2 or SEQ ID NO:5 or SEQ ID NO:6. In other embodiments there is provided a method of treatment of a subject having or suspected of having a neurological disease or condition, the method comprising administering to a subject a therapeutically effective amount of an isolated polypeptide capable of preventing or inhibiting ubiquitination of PTEN. The isolated polypeptide may further comprise a protein transduction domain or other dat moiety. The polypeptide may have an amino acid composition substantially similar to SEQ ID NO: 1 or SEQ ID NO: 2 or SEQ ID NO:5 or SEQ ID NO:6. The neurological disease or condition may be one that is associated with cytotoxic stress or cell death. The neurological disease or condition may be one chosen from the following group: stroke, brain trauma, neurodegenerative disease, Alzheimer's disease, Parkinson's disease, Huntington's disease, and ALS.

The biologically effective amount may be an amount sufficient to prevent cell death. The disease associated with cytotoxic or excitotoxic stress may be selected from spinal cord injury, stroke, traumatic brain injury, multiple sclerosis, Alzheimer's disease, amyotrophic lateral sclerosis (ALS), Parkinson's disease, and Huntington's disease. The disease associated with cytotoxic or excitotoxic stress may be stroke. The PTEN inhibitor may be a polypeptide comprising SEQ ID NO:1. The isolated polypeptide may further include a delivery and targeting (dat) moiety conjugated to the isolated polypeptide. The dat moiety may be selected from one or more of: ligands; receptors; protein transduction domains (PTD); or antibodies. The dat moiety may be a PTD. The PTEN inhibitor may be a polypeptide include an amino acid sequence selected from SEQ ID NO: 2, SEQ ID NO: 5 or SEQ ID NO: 6. The dat moiety may be selected from antennapedia homeodomain, the translocation domain of diphtheria toxin, the translocation domain anthrax toxin, the translocation domain pseudomonas exotoxin a, dermaseptin s4, hsv-1 vp22, pep-1, a tat protein transduction domain, poly-l-lysine, and poly-d-lysine.

Treatment may be of an animal. The animal may be a mammal. The animal may be a human.

Other aspects and features of the present invention would become apparent to those ordinarily skilled in the art by reviewing the following description of specific embodiments of the invention in conjunction with accompanying figures.

DETAILED DESCRIPTION

Figure 1:
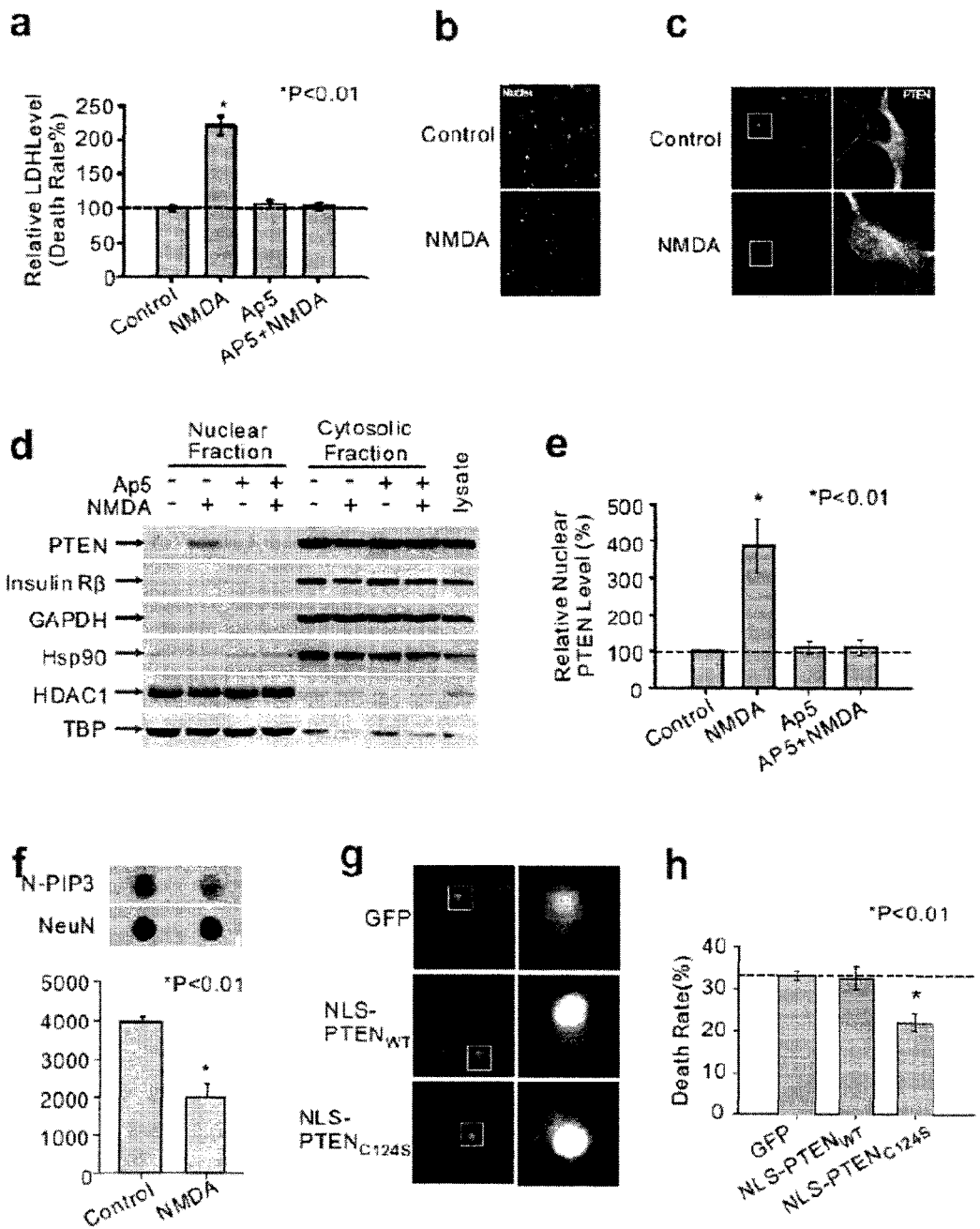
FIG. 1 shows NMDAR activation enhances PTEN nuclear translocation. (a,b) results of both LDH assay (Sigma, #TOX7) and nuclei staining (Hoechst 33342). (c, d, e) immunostaining of endogenous PTEN, and western blotting of subcellular fractions. The purity of the different cellular fractions was confirmed by probing each fraction for corresponding subcellular marker proteins. (f) the level of nuclear PIP3, which is a substrate of nuclear PTEN. (g, h) two mutants of PTEN were over-expressed into cultured hippocampal neurons. One is the phosphatase dead mutant PTENC124S-GFP, and the other is wild-type PTENGFP, while both of them are fused with nuclear localization signal (NLS).

Elucidation of nuclear translocation of PTEN mechanisms in the central nervous system and interference with these processes may provide strategies for the treatment of various diseases associated with cytotoxic stress or excitotoxic stress. For example, stroke, Alzheimer's disease, Parkinson's disease, Huntington's disease, glaucoma, diabetic neuropathy, retinal degenerative diseases, and the like. Provided herein are peptides, polypeptides and compositions thereof for use in the treatment of diseases associated with neuronal shock, injury and/or degradation or with cytotoxicity or excitotoxicity. Excitotoxicity or cytotoxicity may be involved in spinal cord injury, stroke, traumatic brain injury and neurodegenerative diseases of the central nervous system (CNS) such as multiple sclerosis, Alzheimer's disease, amyotrophic lateral sclerosis (ALS), Parkinson's disease, alcoholism or alcohol withdrawal and Huntington's disease. Other common conditions that cause excessive glutamate concentrations around neurons are hypoglycemia and status epilepticus.

Delivery of bioactive molecules such as the polypeptides or peptides described herein, to a cell or cells in a reasonably efficient manner may require more than just the 'dumping' of the naked peptide onto the cell, or administering the naked peptide into the patient or test subject. Agents that enable delivery or targeting of bioactive molecules into cells in a suitable manner so as to provide an effective amount, such as a pharmacologically effective amount are known in the art, and are described in, for example, Dietz et al 2004. *Mol Cell. Neurosci* 27:85-131. The peptides or polypeptides described herein may be conjugated to such a delivery and targeting (dat) moiety or moieties. The term delivery and targeting (dat) moiety as used herein is meant to encompass any moiety that assists in delivering or targeting the peptides or polypeptides described herein to a target cell or tissue or within a target cell or within the cells of a target tissue. Furthermore, a 'dat moiety' may 'assist' in delivery or targeting by virtue of promoting the biological efficacy of the peptides or polypeptides described herein.

Examples of 'dat moieties', may include liposomes, lipid particles, antibodies, receptor ligands, protein transduction domains (PTD), and viral vectors that may be coupled to the PTEN inhibiting peptide or polypeptide as described herein.

For example, where delivery to the brain is desired, isolated peptides or polypeptides described herein may be conjugated to antibodies that bind brain endothelial cell receptors resulting in endocytosis/transcytosis of the receptor and bound ligands (for example, U.S. Pat. No. 7,744,879). Peptides or polypeptides may be conjugated to a PDT, for example the HIV protein TAT (trans-activating transcriptional activator protein), which allows peptides to transverse cell membranes via endocytosis. For example, SEQ ID NO:2 (i.e. KEIVSRNKRRYQED-YGRKKRRQRRR), which is the PTEN K13 interference peptide (underlined), conjugated to the TAT protein transduction domain.

Examples of PTDs include Antennapedia homeodomain (PEREZ et al 1992 *J. Cell Sci* 102:717-722), transportan (POOGA et al 1998 FASEB J 12: 67-77), the translocation domains of diphtheria toxin (STENMARK et al 1991 *J Cell Biol* 113: 1025-1032; WIEDLOCHA et al 1994 *Cell* 76:1039-1051), anthrax toxin (BALLARD et al 1998 *Infect. Immun* 66:615-619; BLANKE et al 1996 *Proc Natl Acad Sci* 93: 8437-8442) and *Pseudomonas* exotoxin A (PRIOR et al 1992 *Biochemistry* 31:3555-3559), protegrin derivatives such as dermaseptin S4 (HARITON-GAZAL et al 2002 *Biochemistry* 41:9208-9214), HSV-1 VP22 (DILBER et al 1999 *Gene Ther.* 6:12-21), PEP-1 (MORRIS et al 2001 *Nature Biotechnol* 19:1173-1176), basic peptides such as poly-L and poly-D-lysine (WOLFERT et al 1996 *Gene Ther.* 3:269-273; RYSER et al 1980 *Cancer* 45:1207-1211; SHEN et al 1978 *Proc Natl Acad Sci* 75:1872-1876), HSP70 (FUJIHARA et al 1999 *EMBO J* 18:411-419) and HIV-TAT (DEMARCHI et al 1996 *J Virol* 70:4427-4437). Other examples and related details of such protein transduction domains are described in DIETZ, supra and references cited therein. Furthermore, to reduce peptide degradation during whole body delivery, peptides may be conjugated to small micelles or liposomes using modified PEG, or subject to end-modifications, such as C-terminal amidation or N-terminal acetylation.

Two distinct types of conjugations are contemplated herein. One type of conjugation can be through noncovalent or attractive binding as with an antigen and antibody or biotin and avidin. Noncovalent coupling is binding between substances through ionic or hydrogen bonding or van der waals forces, and/or their hydrophobic or hydrophilic properties. Alternatively, conjugation may be through covalent, electron-pair bonds or linkages. Many methods and agents for covalent conjugation (or crosslinking) are known and, with appropriate modification, can be used to conjugate the desired substances to the peptide or polypeptide.

The peptides or polypeptides described herein may be further conjugated to a protecting group at either the amino or carboxyl terminus or both. A protecting group may be selected from the group consisting of an acetyl, amide, 3 to 20 carbon alkyl groups, Fmoc, 9-fluoreneacetyl group, 1-fluorenecarboxylic group, 9-fluorenecarboxylic, 9-fluorenone-1-carboxylic group, benzyloxycarbonyl, Xanthyl (Xan), Trityl (Trt), 4-methyltrityl (Mtt), 4-methoxytrityl (Mint), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4dimethyl-2,6-dioxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO), t-butoxymethyl (Bum), t-butoxy (tBuO), t-Butyl (tBu), a propyl group, a butyl group, a pentyl group, a hexyl group, and Trifluoroacetyl (TFA).

The peptides or polypeptides described herein may be further covalently conjugated to a phospholipid comprising a fatty acid selected from the group consisting of propionoyl, butanoyl, pentanoyl, caproyl, heptanoyl, capryloyl, nonanoyl, capryl, undecanoyl, lauroyl, tridecanoyl, myristoyl, pentadecanoyl, palmitoyl, heptadecanoyl, stearoyl, nonadecanoyl, arachidoyl, heniecosanoyl, behenoyl, trucisanoyl, lignoceroyl, myristoleoyl (9-cis), myristelaidoyl (9-trans), palmitoleoyl (9-cis), and palmitelaidoyl (9-trans).

Alternatively or in addition, the peptides or polypeptides described herein may be combined with a pharmaceutically acceptable carrier (or excipient) to form a pharmacological composition. Such 'carriers' may further assist in delivery and targeting or of the polypeptides or peptides described herein either on their own or in conjunction with a dat moiety. Pharmaceutically acceptable carriers may contain one or more physiologically acceptable compound(s) that act, for example, to stabilize the composition or to increase or decrease the absorption of the active agent(s) as desired. Physiologically acceptable compounds may include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers. Accordingly, some overlap may exist between the dat moieties and the carriers described herein. However, generally, the carriers described herein are intended to encompass a larger group of potential entities, which may have little or nothing to do with the specific delivery or targeting of a peptide or polypeptide described herein and may just assist in stabilizing the peptide or polypeptide described herein.

The functional groups conjugated to peptides or polypeptides described herein may be a biological delivery and targeting moiety. For the purposes of this invention, biological delivery and targeting moieties are those that bind to a specific biological substance or site. The biological substance or site that is the intended target of the delivery and targeting moiety may assist in the delivery of the peptides or polypeptides described herein to the tissue or cells of interest. Examples of biological delivery and targeting molecules are described below.

A ligand may function as a delivery and targeting moiety by selectively binding or having a specific affinity for another substance. A ligand may be recognized and bound by a specific binding body or binding partner, or receptor. Examples of ligands suitable for targeting may be selected from antigens, haptens, biotin, biotin derivatives, lectins, galactosamine and fucosylamine moieties, receptors, substrates, coenzymes and cofactors among others.

Another type of delivery and targeting moiety is an antibody, which is defined to include all classes of antibodies, monoclonal antibodies, chimeric antibodies, Fab fractions, fragments and derivatives thereof. Other delivery and targeting moieties may include enzymes, especially cell surface enzymes such as neuraminidases, plasma proteins, avidins, streptavidins, chalones, cavitands, thyroglobulin, intrinsic factor, globulins, chelators, surfactants, organometallic substances, staphylococcal protein A, protein G, cytochromes, lectins, certain resins, and organic polymers.

Delivery and targeting moieties may also include various substances such as any proteins, protein fragments or polypeptides with affinity for the surface of any cells or tissues to be targeted by the peptide or polypeptides described herein (i.e. isolated polypeptide comprising SEQ ID NO:1, wherein the polypeptide has phosphatase and tensin homolog (PTEN) inhibitory activity). These proteins may be produced through recombinant DNA, genetic and molecular engineering techniques know in the art. Of particular use would be any suitable membrane transfer proteins to facilitate the transfer of the peptide or polypeptides described herein to the target cell interior (for example, a PTD as described herein).

Such delivery and targeting moieties may facilitate the transport of the peptides or polypeptides described herein into the cell interior. One such example is U.S. Pat. No. 6,204,054, which describes the use of transcytosis vehicles and enhancers capable of transporting physiologically-active agents across epithelia, endothelia and mesothelia containing the GP60 receptor. The GP60 receptor has been implicated in receptor-mediated transcytosis of albumin across cell barriers. U.S. Pat. No. 6,204,054 exploits GP60 receptor-mediated transcytosis for the transport of physiologically-active agents which do not naturally pass through epithelia, endothelia and mesothelia via the GP60 system. A peptide or polypeptide described herein may be coupled to albumin, albumin fragments, anti-GP60 polyclonal and monoclonal antibodies, anti-GP60 polyclonal and monoclonal antibody fragments, and GP60 peptide fragments to facilitate transport into the cell.

The conjugation to a functional group may also improve other properties of the peptide or polypeptides described herein. Such functional groups are often termed drug carriers and can improve the stability, solubility or biocompatibility of the drug being carried.

For example the solubility of the peptide or polypeptides described herein may be improved by conjugating the peptide or polypeptides described herein to a peptide polymer. The use of polypeptides (containing glutamic acid and aspartic acid, or glutamic acid/alanine, or glutamic acid/asparagine, or glutamic acid/glutamine, or glutamic acid/glycine) as conjugated to drugs to act as carriers to improve the solubility of the drugs and/or their therapeutic efficacy in vivo (U.S. Pat. No. 7,067,494). Similarly, U.S. Pat. No. 5,087,616 describes the use of a biodegradable polymeric carrier to which one or more cytotoxic molecules, such as daunomycin is conjugated. The biodegradable polymeric carrier is specified to be, for example, a homopolymer of polyglutamic acid. Furthermore, U.S. Pat. No. 4,960,790 covalently conjugation to glutamic acid. Alternatively, U.S. Pat. No. 5,420,105 describes the use of polypeptide carriers that are capable of binding one drug or multiple drugs. In accordance with the embodiments described herein the polypeptide carrier may be further attached to a targeting or delivery moiety, such as an antibody or ligand capable of binding to a desired target site in vivo (for example, U.S. Pat. No. 5,420,105).

Similarly, U.S. Pat. No. 6,127,349 describes the use of phospholipids to improve the solubility of peptides and to improve their bio-availability. Similarly, fatty acids could be conjugated to the peptide or polypeptides described herein in order to stabilize the activity of the anti-angiogenic substances. U.S. Pat. No. 6,380,253 describes the conjugation of anti-angiogenic substances (proteins—angiostatin and endostatin etc.) to cis unsaturated fatty acids or polyunsaturated fatty acids to potentiate and stabilize the activity of the anti-angiogenic substances.

Other suitable drug carriers include Polyethylene glycol (PEG) and related polymer derivatives. Such drug-PEG conjugates have been described as improving the circulation time (prolong serum half-life) before hydrolytic breakdown of the conjugate and subsequent release of the bound molecule thus increasing the drugs efficacy. U.S. Pat. No. 6,214,966 describes the use of PEG and related polymer derivatives having weak, hydrolytically unstable linkages near the reactive end of the polymer to conjugate to drugs such as proteins, enzymes and small molecules.

Other physiologically acceptable compounds may include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

The excipients are preferably sterile and generally free of undesirable matter. These compositions may be sterilized and purified by conventional, well-known sterilization and purification techniques.

In therapeutic applications, the compositions described herein may be administered to a subject suffering from one or more symptoms of a disease associated with cytotoxic or excitotoxic stress in an amount sufficient to cure or at least partially prevent or arrest the disease and/or its complications or to help alleviate the symptoms associated therewith. An amount adequate to accomplish this is defined as a "therapeutically effective dose" or "a therapeutically effective amount". Amounts effective for this use will depend upon the severity of the disease and the general state of the subject's health. Single or multiple administrations of the compositions may be administered depending on the dosage and frequency as required and tolerated by the patient. A composition generally would provide a sufficient quantity of the active peptide or polypeptides described herein to effectively treat (for example, to at least ameliorate one or more symptoms) in the subject.

The concentration of peptide or polypeptides described herein can vary widely, and may be selected primarily based on fluid volumes, viscosities, body weight and the like in accordance with the particular mode of administration selected and the subject's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. In certain embodiments, dosages may range from about 20 mg to about 50 mg given orally twice daily. It will be appreciated that such dosages may be varied to optimize a therapeutic regimen in a particular subject or group of subjects.

In certain embodiments, the peptide or polypeptides described herein may be administered orally (e.g. via a tablet) or as an injectable in accordance with standard methods well known to those of skill in the art. In other embodiments, peptide or polypeptides described herein, may also be delivered through the skin using conventional transdermal drug delivery systems, i.e., transdermal "patches" wherein the active agent(s) are typically contained within a laminated structure that serves as a peptide or polypeptides delivery device to be affixed to the skin. In such a structure, the composition is typically contained in a layer, or "reservoir", underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

Other formulations for topical drug delivery may include, but are not limited to, ointments and creams. Ointments are semisolid preparations which are typically based on petrolatum or other petroleum derivatives. Creams containing the selected active agent, are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

The peptide or polypeptides described herein may be administered orally. Peptide or polypeptide delivery may be enhanced by the use of protective excipients. This is typically accomplished either by complexing the polypeptide with a composition to render it resistant to acidic and enzymatic hydrolysis or by packaging the polypeptide in an appropriately resistant carrier such as a liposome. Means of protecting polypeptides for oral delivery are well known in the art.

Elevated serum half-life can be maintained by the use of sustained-release protein "packaging" systems. Such sustained release systems are well known to those of skill in the art. A PROLEASE™ biodegradable microsphere delivery system for proteins and peptides is known (for example, Tracy (1998) Biotechnol. Prog. 14: 108; Johnson et al. (1996), Nature Med. 2: 795; Herbert et al. (1998), Pharmaceut. Res. 15, 357), wherein a dry powder composed of biodegradable polymeric microspheres containing the protein in a polymer matrix that can be compounded as a dry formulation with or without other agents. This system was specifically designed to achieve a high protein encapsulation efficiency while maintaining protein integrity. The resulting powder contains the solid form of the peptide or polypeptide, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., −40° C.). During encapsulation, the peptide or polypeptide may be maintained in the solid state in the absence of water, thus minimizing water-induced conformational mobility of the peptide or polypeptide, preventing peptide or polypeptide degradation reactions that include water as a reactant, and avoiding organic-aqueous interfaces where proteins may undergo denaturation.

In certain embodiments, the peptides or polypeptides may be administered in conjunction with one or more lipids. The lipids can be formulated as an excipient to protect and/or enhance transport/uptake of the peptide or polypeptide or they can be administered separately.

The lipids can be formed into liposomes that encapsulate the peptides or polypeptides described herein and/or they can be complexed/admixed with the peptides or polypeptides and/or they can be covalently coupled to the peptides or polypeptides described herein. Methods of making liposomes and encapsulating reagents are well known to those of skill in the art (see, e.g., Martin and Papahadjopoulos (1982) J. Biol. Chem., 257: 286-288; Papahadjopoulos et al. (1991) Proc. Natl. Acad Sci. USA, 88: 11460-11464; Huang et al. (1992) Cancer Res., 52:6774-6781; Lasic et al. (1992) FEBS Lett., 312: 255-258, and the like).

The foregoing formulations and administration methods are intended to be illustrative and not limiting. It will be appreciated that, using the teaching provided herein, other suitable formulations and modes of administration can be readily devised.

Additional pharmacologically active agents may be delivered along with the primary active agents, e.g., the peptides or polypeptides described herein. The peptide or polypeptide may be conjugated to another pharmaceutically active agent to enhance the therapeutic effect on the target cell or tissue by delivering a second compound with a similar or complimentary activity. In one embodiment, such agents include, but are not limited to agents that reduce the risk of a stroke or ischemic injury and/or complications thereof. Such agents include, but are not limited to Anticoagulants (for example, Acenocoumarol, Coumatetralyl, Dicoumarol, Ethyl biscoumacetate, Phenprocoumon, Warfarin, Clorindione, Diphenadione, Phenindione, Tioclomarol, Bemiparin, Certoparin, Dalteparin, Enoxaparin, Nadroparin, Parnaparin, Reviparin, Tinzaparin, Fondaparinux, Idraparinux, Danaparoid, Sulodexide, Dermatan sulfate, Apixaban, Betrixaban, Edoxaban, Otamixaban, Rivaroxaban, Hirudin, Bivalirudin, Lepirudin, Desirudin, Argatroban, Dabigatran, Melagatran, Ximelagatran, REG1, Defibrotide, Ramatroban, Antithrombin III, and Drotrecogin alfa), Antiplatelet drugs (for example, Abciximab, Eptifibatide, Tirofiban, Clopidogrel, Prasugrel, Ticlopidine, Ticagrelor, Beraprost, Prostacyclin, Iloprost, Treprostinil, Acetylsalicylic acid/Aspirin, Aloxiprin, Carbasalate calcium, Indobufen, Triflusal, Dipyridamole, Picotamide, Terutroban, Cilostazol, Dipyridamole, Triflusal, Cloricromen, Ditazole), and Thrombolytic and Firbrinolytic drugs (for example, tissue plasminogen activator (tPA) or recombinant tissue plasminogen activator (rtPA) such as Alteplase, Reteplase, Tenecteplase, Urokinase, Saruplase, Streptokinase, Anistreplase, Monteplase, Ancrod, Fibrinolysin, and Brinase), and the like.

Any terms not directly defined herein shall be understood to have the meanings commonly associated with them as understood within the art of the invention. As employed throughout the specification, the following terms, unless otherwise indicated, shall be understood to have the following meanings.

As used herein, 'peptide' or 'polypeptide' may be used interchangeably, and generally refer to a compound comprised of at least two amino acid residues covalently linked by peptide bonds or modified peptide bonds. However, when specifically used with the phrase "as described herein" or "the isolated polypeptide comprising SEQ ID NO:1", it is meant to comprise an amino acid sequence of the PTEN K13 interference peptide represented by SEQ ID NO:1 (i.e. KEIVSRNKRRYQED), wherein the polypeptide has phosphatase and tensin homolog (PTEN) inhibitory activity. Modified peptide bonds may include for example peptide isosteres (modified peptide bonds) that may provide additional desired properties to the peptide, such as increased half-life. A peptide may comprise at least two amino acids. The amino acids comprising a peptide or polypeptide described herein may also be modified either by natural processes, such as posttranslational processing, or by chemical modification techniques which are well known in the art. Modifications can occur anywhere in a peptide, including the peptide backbone, the amino acid side-chains and the amino or carboxyl termini. It is understood that the same type of modification may be present in the same or varying degrees at several sites in a given peptide.

As used herein a 'vector' refers to a polynucleotide compound used for introducing exogenous or endogenous polynucleotide into host cells. A vector comprises a nucleotide sequence, which may encode one or more polypeptide molecules. Plasmids, cosmids, viruses and bacteriophages, in a natural state or which have undergone recombinant engineering, are non-limiting examples of commonly used vectors to provide recombinant vectors comprising at least one desired isolated polynucleotide molecule.

In the case of peptides or proteins, or in the case of nucleic acids defined according to a encoded peptide or protein correspondence includes a peptide having at least about 80% identity, more preferably at least about 90% identity, even more preferably about 95% and most preferably at least about 98-99% identity to a specified peptide or polypeptide or protein or portion thereof.

Embodiments described herein encompass an isolated polypeptide comprising at least 90% identity to SEQ ID NO:1, provided that the lysine (K) at position 8 of SEQ ID NO:1 or an equivalent position (also known as K13 relative to the full length PTEN protein—see SEQ ID NO:7) is not altered to preserve the ubiquitination site.

The term "identity" as used herein refers to the measure of the identity of sequence between two peptides or between two nucleic acids molecules. Identity can be determined by comparing a position in each sequence which may be a line for purposes of comparison. Two amino acid or nucleic acid sequences are considered substantially identical if they share at least about 85% sequence identity, or at least about 86% sequence identity, or at least about 87% sequence identity, or at least about 88% sequence identity, or at least about 89% sequence identity, or at least about 90% sequence identity. Alternatively, two amino acid or nucleic acid sequences are considered substantially identical if they share at least about 91% sequence identity, or at least about 92% sequence identity, or at least about 93% sequence identity, or at least about 94% sequence identity, or at least about 95% sequence identity, or at least about 96% sequence identity, or at least about 97% sequence identity, or at least about 98% sequence identity, or at least about 99% sequence identity.

Sequence identity may be determined by the BLAST algorithm currently is use and which was originally described in Altschul et al. (1990) J. Mol. Biol. 215:403-410. The BLAST algorithm may be used with the published default settings. When a position in the compared sequence is occupied by the same base or amino acid, the molecules are considered to have shared identity at that position. The degree of identity between sequences is a function of the number of matching positions shared by the sequences and the degree of overlap between the sequences. Furthermore, when considering the degree of identity with SEQ ID NO:1, it is intended that the equivalent 14 amino acids (for example, the corresponding 7 amino acids preceding the lysine (K) at position 8 and the 6 amino acids following the lysine (K) at position 8 be compared to SEQ ID NO:1. Additional sequences (i.e. other than those corresponding to the 14 amino acids of SEQ ID NO:1), are not intended to be considered when determining the degree of identity with SEQ ID NO:1.

Furthermore, the isolated polypeptide comprising SEQ ID NO:1 or a sequence comprising 14 amino acid having at least 90% identity to SEQ ID NO:1 may have less than or equal to 59 amino acids. Alternatively, the isolated polypeptide may have 55 amino acids, or the isolated polypeptide may have 54 amino acids, or the isolated polypeptide may have 53 amino acids, or the isolated polypeptide may have 52 amino acids, or the isolated polypeptide may have 51 amino acids, or the isolated polypeptide may have 50 amino acids, or the isolated polypeptide may have 49 amino acids, or the isolated polypeptide may have 48 amino acids, or the isolated polypeptide may have 47 amino acids, or the isolated polypeptide may have 46 amino acids, or the isolated polypeptide may have 45 amino acids, or the isolated polypeptide may have 44 amino acids, or the isolated polypeptide may have 43 amino acids, or the isolated polypeptide may have 42 amino acids, or the isolated polypeptide may have 41 amino acids, or the isolated polypeptide may have 40 amino acids, or the isolated polypeptide may have 39 amino acids, or the isolated polypeptide may have 38 amino acids, or the isolated polypeptide may have 37 amino acids, or the isolated polypeptide may have 36 amino acids, or the isolated polypeptide may have 35 amino acids, or the isolated polypeptide may have 34 amino acids, or the isolated polypeptide may have 33 amino acids, or the isolated polypeptide may have 32 amino acids, or the isolated polypeptide may have 31 amino acids, or the isolated polypeptide may have 30 amino acids, or the isolated polypeptide may have 29 amino acids, or the isolated polypeptide may have 28 amino acids, or the isolated polypeptide may have 27 amino acids, or the isolated polypeptide may have 26 amino acids, or the isolated polypeptide may have 25 amino acids, or the isolated polypeptide may have 24 amino acids, or the isolated polypeptide may have 23 amino acids, or the isolated polypeptide may have 22 amino acids, or the isolated polypeptide may have 21 amino acids, or the isolated polypeptide may have 20 amino acids, or the isolated polypeptide may have 19 amino acids, or the isolated polypeptide may have 18 amino acids, or the isolated polypeptide may have 17 amino acids, or the isolated polypeptide may have 16 amino acids, or the isolated polypeptide may have 15 amino acids, or the isolated polypeptide may have 14 amino acids, or the isolated polypeptide may have 13 amino acids, or the isolated polypeptide may have 12 amino acids, or the isolated polypeptide may have 11 amino acids, or the isolated polypeptide may have 10 amino acids. Alternatively, the isolated polypeptide may have between 10 and 50 amino acids, or the isolated polypeptide may have between 11 and 50 amino acids, or the isolated polypeptide may have between 12 and 50 amino acids, or the isolated polypeptide may have between 13 and 50 amino acids, or the isolated polypeptide may have between 14 and 50 amino acids, or the isolated polypeptide may have between 13 and 45 amino acids, or the isolated polypeptide may have between 13 and 40 amino acids, or the isolated polypeptide may have between 13 and 35 amino acids, or the isolated polypeptide may have between 13 and 30 amino acids, or the isolated polypeptide may have between 13 and 25 amino acids, or the isolated polypeptide may have between 13 and 20 amino acids, or the isolated polypeptide may have between 14 and 50 amino acids, or the isolated polypeptide may have between 14 and 35 amino acids, or the isolated polypeptide may have between 14 and 30 amino acids, or the isolated polypeptide may have between 14 and 29 amino acids, or the isolated polypeptide may have between 14 and 28 amino acids, or the isolated polypeptide may have between 14 and 27 amino acids, or the isolated polypeptide may have between 14 and 26 amino acids, or the isolated polypeptide may have between 14 and 25 amino acids, or the isolated polypeptide may have between 14 and 24 amino acids, or the isolated polypeptide may have between 14 and 23 amino acids, or the isolated polypeptide may have between 14 and 22 amino acids, or the isolated polypeptide may have between 14 and 21 amino acids, or the isolated polypeptide may have between 14 and 20 amino acids, or the isolated polypeptide may have between 14 and 19 amino acids, or the isolated polypeptide may have between 14 and 18 amino acids, or the isolated polypeptide may have between 14 and 17 amino acids, or the isolated polypeptide may have between 14 and 16 amino acids, or the isolated polypeptide may have between 14 and 15 amino acids.

It will be appreciated by a person of skill in the art the aspects of the individual amino acids in a peptide or polypeptide described herein may be substituted. Amino acid sequence identity may be computed by using the BLASTP and TBLASTN programs which employ the BLAST (basic local alignment search tool) 2.0 algorithm. Techniques for computing amino acid sequence similarity or identity are well known to those skilled in the art, and the use of the BLAST algorithm is described in ALTSCHUL et al. 1990, *J Mol. Biol.* 215: 403-410 and ALTSCHUL et al. (1997), *Nucleic Acids Res.* 25: 3389-3402.

Furthermore, it will be appreciated by a person of skill in the art that certain substitutions are more likely to result in retention of activity. For example, amino acids may be described as, for example, polar, non-polar, acidic, basic, aromatic or neutral. A polar amino acid is an amino acid that may interact with water by hydrogen bonding at biological or near-neutral pH. The polarity of an amino acid is an indicator of the degree of hydrogen bonding at biological or near-neutral pH. Examples of polar amino acids include serine, proline, threonine, cysteine, asparagine, glutamine, lysine, histidine, arginine, aspartate, tyrosine and glutamate. Examples of non-polar amino acids include glycine, alanine, valine leucine, isoleucine, methionine, phenylalanine, and tryptophan. Acidic amino acids have a net negative charge at a neutral pH. Examples of acidic amino acids include aspartate and glutamate. Basic amino acids have a net positive charge at a neutral pH. Examples of basic amino acids include arginine, lysine and histidine. Aromatic amino acids are generally nonpolar, and may participate in hydrophobic interactions. Examples of aromatic amino acids include phenylalanine, tyrosine and tryptophan. Tyrosine may also participate in hydrogen bonding through the hydroxyl group on the aromatic side chain. Neutral, aliphatic amino acids are generally nonpolar and hydrophobic. Examples of neutral amino acids include alanine, valine, leucine, isoleucine and methionine. An amino acid may be described by more than one descriptive category. Amino acids sharing a common descriptive category may be substitutable for each other in a peptide.

Nomenclature used to describe the peptides or polypeptides may follow the conventional practice where the amino group is presented to the left and the carboxy group to the right of each amino acid residue. In the sequences representing selected specific embodiments of the present invention, the amino- and carboxy-terminal groups, although not specifically shown, will be understood to be in the form they would assume at physiologic pH values, unless otherwise specified. In the amino acid structure formulae, each residue may be generally represented by a one-letter or three-letter designation, corresponding to the trivial name of the amino acid, in accordance TABLE 1.

TABLE 1

Nomenclature and abbreviations of the 20 standard L-amino acids commonly found in naturally occurring peptides.

| Full name | Three-letter abbreviation | One-letter abbreviation |
| --- | --- | --- |
| Alanine | Ala | A |
| Cysteine | Cys | C |
| Aspartic acid | Asp | D |
| Glutamic acid | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asp | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | T |

The hydropathy index of an amino acid is a scale indicating the tendency of an amino acid to seek out an aqueous environment (negative value) or a hydrophobic environment (positive value) (KYTE & DOOLITTLE 1982. *J Mol Biol* 157:105-132). Hydropathy indices of the standard amino acids include alanine (1.8), arginine (−4.5), asparagine (−3.5), aspartic acid (−3.5), cysteine (2.5), glutamine (−3.5), glutamic acid (−3.5), glycine (−0.4), histidine (−3.2), isoleucine (4.5), leucine (3.8), lysine (−3.9), methionine (1.9), phenylalanine (2.8), proline (−1.6), serine (−0.8), threonine (−0.7), tryptophan (−0.9), tyrosine (−1.3), and valine (4 2) Amino acids with similar hydropathy indices may be substitutable for each other in a peptide.

Amino acids contained within the peptides or polypeptides described herein will be understood to be in the L- or D-configuration. In peptides and peptidomimetics the D-amino acids may be substitutable for L-amino acids. Amino acids contained within the peptides or polypeptides, and particularly at the carboxy-or amino-terminus, may be modified by methylation, amidation, acetylation or substitution with other chemical groups which may change the circulating half-life of the peptide without adversely affecting their biological activity. Additionally, a disulfide linkage may be present or absent in the peptides or polypeptides described herein.

Nonstandard amino acids may occur in nature, and may or may not be genetically encoded. Examples of genetically encoded nonstandard amino acids include selenocysteine, sometimes incorporated into some proteins at a UGA codon, which may normally be a stop codon, or pyrrolysine, sometimes incorporated into some proteins at a UAG codon, which may normally be a stop codon. Some nonstandard amino acids that are not genetically encoded may result from modification of standard amino acids already incorporated in a peptide, or may be metabolic intermediates or precursors, for example. Examples of nonstandard amino acids include 4-hydroxyproline, 5-hydroxylysine, 6-N-methyllysine, gamma-carboxyglutamate, desmosine, selenocysteine, ornithine, citrulline, lanthionine, 1-aminocyclopropane -1-carboxylic acid, gamma-aminobutyric acid, carnitine, sarcosine, or N-formylmethionine. Synthetic variants of standard and non-standard amino acids are also known and may include chemically derivatized amino acids, amino acids labeled for identification or tracking, or amino acids with a variety of side groups on the alpha carbon. Examples of such side groups are known in the art and may include aliphatic, single aromatic, polycyclic aromatic, heterocyclic, heteronuclear, amino, alkylamino, carboxyl, carboxamide, carboxyl ester, guanidine, amidine, hydroxyl, alkoxy, mercapto-, alkylmercapto-, or other heteroatom-containing side chains. Other synthetic amino acids may include alpha-imino acids, non-alpha amino acids such as beta-amino acids, des-carboxy or des-amino acids. Synthetic variants of amino acids may be synthesized using general methods known in the art, or may be purchased from commercial suppliers, for example RSP AMINO ACIDS LLC™(Shirley, MA).

'Cytotoxic stress' as used herein is meant to encompass a broad range of cellular stresses including pathologic changes in response to excessive levels of cytotoxic oxidants and free radicals in a cells environment (for example, oxidative stress), may be immune mediated, may also include excitotoxic stresses.

'Excitotoxic stress' as used herein is an important component of disorders such as stroke and other neurodegenerative diseases. There is evidence that the toxic effects of excitotoxic stress may be exerted through mechanisms that result in both acute and delayed forms of cell death, when receptors for the excitatory neurotransmitter glutamate (glutamate receptors) such as the NMDA receptor and AMPA receptor are overactivated. Excitotoxins like NMDA and kainic acid which bind to these receptors, as well as pathologically high levels of glutamate, can cause excitotoxicity by allowing high levels of calcium ions[2] ($Ca^{2+}$) to enter the cell. $Ca^{2+}$ influx into cells can activate a number of enzymes, including phospholipases, endonucleases, and proteases such as calpain. These enzymes are capable of damaging cell structures like the cytoskeleton, cell membranes, and DNA. Excitotoxicity may be involved in spinal cord injury, stroke, traumatic brain injury and neurodegenerative diseases of the central nervous system (CNS) such as multiple sclerosis, Alzheimer's disease, amyotrophic lateral sclerosis (ALS), Parkinson's disease, alcoholism or alcohol withdrawal and Huntington's disease.

As used herein 'isolated', is meant to encompass a substance (such as, a polynucleotide or polypeptide or peptide) has been substantially separated or purified away from other components, such as biological components, with which it would otherwise be associated, for example in vivo, so that the isolated substance may be itself be manipulated or processed. The term 'isolated' therefore includes substances purified by purification methods known in the art, as well as substances prepared by recombinant expression in a host, as well as chemically synthesized substances. In some embodiments, a compound is 'isolated' when it is separated from the components that naturally accompany it so that it is at least 60%, more generally 75% or over 90%, by weight, of the total relevant material in a sample. Thus, for example, a polypeptide that is chemically synthesized or produced by recombinant technology may be generally substantially free from its naturally associated components. A polynucleotide may be substantially pure when it is not immediately contiguous with (i.e., covalently linked to) the coding sequences with which it is normally contiguous in the naturally occurring genome of the organism from which the DNA of the invention is derived. An isolated compound can be obtained, for example, by extraction from a natural source; by expression of a recombinant nucleic acid molecule encoding a polypeptide compound; or by chemical synthesis. Purity can be measured using any appropriate method such as column chromatography, gel electrophoresis or HPLC.

The term 'recombinant' is meant to encompass something that has been recombined, so that when made in reference to a nucleic acid construct (for example, a polynucleotide) the term refers to a molecule that is comprised of nucleic acid sequences that are joined together or produced by means of molecular biological techniques. The term 'recombinant' when made in reference to a protein or a polypeptide or a peptide refers to a protein or polypeptide or peptide molecule, which is expressed using a recombinant nucleic acid construct created by means of molecular biological techniques. Recombinant nucleic acid constructs may include a nucleotide sequence, which is ligated to, or is manipulated to become ligated to, a nucleic acid sequence to which it is not ligated in nature, or to which it is ligated at a different location in nature. A recombinant nucleic acid construct, therefore, indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of transformation of the host cells, or as the result of subsequent recombination events.

Polypeptides or peptides or peptide analogues may be synthesised by chemical techniques known in the art, for example, by automated synthesis using solution or solid phase synthesis methodology. Automated peptide synthesisers are commercially available and use techniques well known in the art. Polypeptides or peptides and peptide analogues can also be prepared using recombinant DNA technology using methods such as those described in, for example, SAMBROOK J. AND RUSSELL D. (2000) Molecular Cloning: A Laboratory Manual (Third Edition)

Cold Spring Harbor Laboratory, Cold Spring Harbor Laboratory Press, Cold Spring Harbor, N.Y.) or AUSUBEL et al. (Current Protocols in Molecular Biology, John Wiley & Sons, 1994).

As used herein a 'subject' refers to an animal, such as a bird or a mammal. Specific animals include rat, mouse, dog, cat, cow, sheep, horse, pig or primate. A subject may further be a human. A subject may further be a transgenic animal. A subject may further be a rodent, such as a mouse or a rat.

The term 'NMDA' refers to N-methyl-D-asparate, and 'NMDAR' refers to NMDA receptor(s). NMDAR is an ionotropic receptor for glutamate. NMDA is a selective specific agonist of NMDAR. Activation of NMDA receptors results in the opening of an ion channel that is nonselective to cations. This allows flow of Na+ and small amounts of Ca2+ ions into the cell and K+ out of the cell. Calcium flux through NMDARs is thought to play a critical role in synaptic plasticity, a cellular mechanism for learning and memory. The NMDA receptor forms a heterodimer between NR1 and NR2 subunits. There are numerous NR1 and NR2 isoforms that exist. The NRI isoforms are generated from different alternative splicing of the GRIN1 (also called NMDAR1—EntrezGene ID: 2902). The NR2 isoforms are generated from four genes—GRIN2A (NMDAR2A—EntrezGene ID: 2903), GRIN2B (NMDAR2B—EntrezGene ID: 2904), GRIN2C (NMDAR2C—EntrezGene ID: 2905), and GRIN2D (NMDAR2D—EntrezGene ID: 2906). A related gene family of NR3 A and B subunits have an inhibitory effect on receptor activity. Multiple receptor isoforms with distinct brain distributions and functional properties arise by selective splicing of the NR1 transcripts and differential expression of the NR2 subunits.

The term 'PTEN' refers to the phosphatase and tensin homolog enzyme—the human form of this protein is the product of EntrezGene ID: 5728 and which may have an amino acid sequence composition corresponding to GenPept Accession: P60484.1. Other non-human homologs are easily identified using known methods, for instance BLAST search, and are considered to be within the scope of the invention. PTEN protein acts as a phosphatase to dephosphorylate phosphatidylinositol (3,4,5)-trisphosphate (PtdIns (3,4,5)P3 or PIP3). PTEN specifically catalyses the dephosphorylation of the 3' phosphate of the inositol ring in PIP3, resulting in the biphosphate product PIP2 (PtdIns(4,5)P2). This dephosphorylation is important because it results in inhibition of the AKT signaling pathway.

A representative PTEN amino acid sequence is shown in TABLE 2 below (AAC08699.1 GI:2197039), with SEQ ID NO:1 underlined.

TABLE 2

PTEN AMINO ACID SEQUENCE (SEQ ID NO: 7)
MTAI IKEIVSRNKRRYQEDGFDLDLTYIYPNI IAMGFPAERLEGVYRNNI

DDVVRFLDSKHKNHYKIYNLCAERHYDTAKFNCRVAQYPFEDHNPPQLEL

IKPFCEDLDQWLSEDDNHVAAIHCKAGKGRTGVMICAYLLHRGKFLKAQE

ALDFYGEVRTRDKKGVTIPSQRRYVYYYSYLLKNHLDYRPVALLFHKMME

ETIPMFSGGTCNPQFVVCQLKVKIYSSNSGPTRREDKFMYFEFPQPLPVC

GDIKVEFFHKQNKMLKKDKMFHFWVNTFFIPGPEETSEKVENGSLCDQEI

DSICSIERADNDKEYLVLTLTKNDLDKANKDKANRYFSPNFKVKLYFTKT

VEEPSNPEASSSTSVTPDVSDNEPDHYRYSDTTDSDPENEPFDEDQHTQI

TKV

Amino acids contained within the peptides or polypeptides described herein will be understood to be in the L- or D-configuration. D-amino acids may be substitutable for L-amino acids. Amino acids contained within the peptides or polypeptides described herein, and particularly at the carboxy-or amino-terminus, may be modified by methylation, amidation, acetylation or substitution with other chemical groups which may change the circulating half-life of the peptide or polypeptide without adversely affecting their biological activity. Additionally, a disulfide linkage may be present or absent.

Nonstandard amino acids may occur in nature, and may or may not be genetically encoded. Examples of genetically encoded nonstandard amino acids include selenocysteine, sometimes incorporated into some proteins at a UGA codon, which may normally be a stop codon, or pyrrolysine, sometimes incorporated into some proteins at a UAG codon, which may normally be a stop codon. Some nonstandard amino acids that are not genetically encoded may result from modification of standard amino acids already incorporated in a peptide, or may be metabolic intermediates or precursors, for example. Examples of nonstandard amino acids include 4-hydroxyproline, 5-hydroxylysine, 6-N-methyllysine, gamma-carboxyglutamate, desmosine, selenocysteine, ornithine, citrulline, lanthionine, 1-aminocyclopropane-1-carboxylic acid, gamma-aminobutyric acid, carnitine, sarcosine, or N-formylmethionine. Synthetic variants of standard and non-standard amino acids are also known and may include chemically derivatized amino acids, amino acids labeled for identification or tracking, or amino acids with a variety of side groups on the alpha carbon. Examples of such side groups are known in the art and may include aliphatic, single aromatic, polycyclic aromatic, heterocyclic, heteronuclear, amino, alkylamino, carboxyl, carboxamide, carboxyl ester, guanidine, amidine, hydroxyl, alkoxy, mercapto-, alkylmercapto-, or other heteroatom-containing side chains. Other synthetic amino acids may include alpha-imino acids, non-alpha amino acids such as beta-amino acids, des-carboxy or des-amino acids. Synthetic variants of amino acids may be synthesized using general methods known in the art, or may be purchased from commercial suppliers, for example RSP Amino Acids LLC (Shirley, Mass.).

The term 'medicament' as used herein refers to a composition that may be administered to a subject and is capable of producing an effect in the subject. The effect may be chemical, biological or physical, and subject may be human, or a non-human animal, such as a rodent or transgenic mouse, or a dog, cat, cow, sheep, horse, hamster, guinea pig, rabbit or pig. The medicament may comprise the peptide or polypeptide described herein alone or in combination with a pharmaceutically acceptable excipient.

The term 'antibody' as used herein refers to immune system proteins, also called immunoglobulins, produced in response to foreign substances (antigens). Antibodies typically contain two heavy chains and two light chains, which are joined. Variability in the structure of these chains provides antigen specificity (i.e. allows individual antibodies to recognize specific antigens). The term antibody may include polyclonal and monoclonal antibodies, chimeric, single chain, or humanized antibodies, as well as Fab or F(ab)2 fragments, including the products of an Fab or other immunoglobulin expression library. Methods of making such antibodies or fragments are known in the art and may be found in, for example HARLOW, E and LANE D. Antibodies: A Laboratory Manual. 1988. Cold Spring Harbor Laboratory Press. Antibodies according to some embodiments of the invention may also be intracellular antibodies, sometimes referred to as intrabodies. Methods for designing, making and/or using such antibodies has been described in the art, for instance (Lecerf et al. 2001; Hudson and Souriau 2003). Selection or identification of specific peptides for use as epitopes for production of antibodies that differentiate between proteins, or isoforms of proteins may be made using sequence comparisons—one of skill in the art will be able to identify suitable peptide or protein sequences that may be useful for producing antibodies with the desired selectivities. Polyclonal antibodies are antibodies that are derived from different B-cell lines. In certain embodiments, there are provided antibodies raised against or that bind to a polypeptide having an amino acid composition substantially similar to SEQ ID NO: 1.

The Role of PTEN in Neurons and in Neurological Conditions or Diseases

Described herein are previously unknown aspects of PTEN in neuronal cells, and thus provided novel compositions and methods for prevention and/or treatment of several neurological conditions or diseases. PTEN is reported to have a role in cancer. In these studies, two lysine residues, located at amino acid sequence position 13 and 289 (K13 and K289) have been identified as ubiquitination sites that play a role in the nuclear translocation of the protein. Mutation of either of these sites has been demonstrated to be sufficient to cause a highly significant decrease in nuclear translocation of PTEN. To date, there has been no study on the role of ubiquitination in the nuclear translocation of PTEN in neuronal cells. As described herein, the role of ubiquitination in the translocation of PTEN in neuronal cells is different in such neuronal cells as compared to previously studied cell types.

As shown herein, activation of NMDA receptor, NMDAR, enhanced the nuclear localization of PTEN in cultured neurons, and reduced the level of nuclear PIP3, which is a substrate of nuclear PTEN. The phosphatase activity of PTEN was shown to be significant for NMDA based excitotoxicity—knocking out this phosphatase activity improved survival in cells after treatment with NMDA. When ubiquitination was blocked at either the K13 or K289 sites, it was found that only blocking the K13 site, either by mutation or using an interfering peptide, caused a reduction of nuclear translocation of PTEN and improvement of neuronal cell survival. This result is unexpected and differs from the literature, in which it is taught that disruption of either K13 or K289 ubiquitination site is sufficient to prevent nuclear translocation of PTEN. K13 interference peptide administered to rats using an accepted ischemia stroke model, demonstrated significantly improved post-stroke effects, including reduced infarct volumes, improved glucose metabolic activity, and improved long term motor recovery.

In certain aspects of the invention, there is provided a polyneptide composition having an amino acid composition substantially similar to

```
                                    SEQ ID NO: 1
    (KEIVSRNKRRYQED)
    or

SEQ ID NO: 2
    (KEIVSRNKRRYQED-YGRKKRRQRRR).
```

The following examples are provided for illustrative purposes, and are not intended to be limiting, as such.

Methods

Primary Culture of Cortical Neurons

Dissociated cultures of rat cortical or hippocampal neurons were prepared from 18-d-old Sprague Dawley rat embryos as described previously (Mielke and Wang 2005). To obtain mixed cultures enriched with neurons, uridine (10 µM) and 5-Fluor-2'-deoxyuridine (10 µM) were added to the culture medium at 3 d in vitro (DIV) and maintained for 48 h to inhibit non-neuronal cell proliferation before the cultures were returned to the normal culture medium. Mature neurons (12-14 DIV) were used for experiments.

Experimental in Vitro Excitotoxicity Insults

In order to induce excitotoxicity, 12-14 DIV cultured neurons were washed and transferred to Mg2+-free extracellular solution (ECS) containing the following (in mM): 25 HEPES acid, 140 NaCl, 33 glucose, 5.4 KCl, and 1.3 CaCl2, with pH 7.35 and osmolarity 320-330 mOsm. ECS and subjected to NMDA-induced excitotoxicity (20 µM NMDA, 10 µM glycine, 60 mM at room temperature) or any other experimental conditions as indicated in the texts. Cells were then washed twice with normal ECS, and returned to the original growth conditions until additional assay.

Nuclear Extract Isolation

Nuclear extracts were isolated from control and NMDA-treated cell cultures (108 cells) using the PANOMICS™ nuclear extraction kit (PANOMICS™; catalog number AY2002) as recommended by the manufacturer.

Western Blotting

For western blotting, 10 µg of the nuclear extract or 40 µg of total cell lysate (solubilized by 1% SDS, 1mM EGTA, 1mM EDTA, 1mM DTT, 2mM sodium orthovanadate, and protease inhibitors cocktail in PBS) from each treatment condition was separated with SDS-PAGE, transferred onto a polyvinylidene difluoride (PVDF) membrane, and probed with the relevant antibodies. For sequential re-probing of the same blots, the membranes were stripped of the initial primary and secondary antibodies and subjected to immunoblotting with another target antibody. Blots were developed using enhanced chemiluminescence detection (AMERSHAM™). Band intensities were quantified using NIH IMAGEJ™ software and normalized to the quantity of a nuclear marker or β-tubulin in each sample lane.

Assessment of Neuronal Death

Necrotic neuronal death was quantified by measuring lactate dehydrogenase (LDH) release 20 h after treatments using a CYTO TOX™ 96 assay kit (PROMEGA™, Madison, WI). Absorbance readings were measured using a spectrophotometric microplate reader. Apoptotic neuronal death was determined by visualizing the nucleus condensation and fragmentation of neurons stained with HOECHST-33342™. Images were taken with a LEICA DMIRE2™ fluorescence microscope. Cells with condensed or fragmented chromatin were considered apoptotic. These observations were quantified by double-blind counting of apoptotic and total neurons in each visual field and expressed as percentage apoptosis. Data analyses were performed according to the instructions of the manufacturer. Data are expressed as the difference in apoptosis relative to control and are expressed as a percentage.

In Vivo Ischemia/Reperfusion Brain Model and PTEN Peptide Injection

Adult male Sprague-Dawley rats (weight 200 g) were used in this study. All surgical procedures were performed using sterile/aseptic techniques in accordance with Institutional guidelines. Rats were anesthetized with chloral hydrate (0.4 g/kg IP) and subjected to cerebral ischemia. Ligation of the right middle cerebral artery (MCA) and bilateral common carotids arteries (CCAs) was performed by methods described previously (Shyu et al. 2005). The CCAs were clamped with non-traumatic arterial clips. The right MCA was ligated with a 10-0 nylone suture. After 90 min of ischemia, the suture on the MCA and the arterial clips on the CCAs were removed to allow reperfusion. Core body temperature was monitored with a thermistor probe (HEWLETT-PACKARD™ Model 21090A probe, HEWLETT-PACKARD COMPANY™, Andover, MA), and maintained at 37° C. with a heating pad during anesthesia. After recovery from anesthesia, rat body temperature was maintained at 37° C. with a heat lamp. Experimental rats were subdivided into five groups receiving different types of interference peptides, all fused to a TAT protein transduction domain (PTEN-K13 (SEQ ID NO: 2) 2 hrs or 6 hrs, PTEN-K13R (SEQ ID NO: 3), PTEN-K289 (SEQ ID NO: 4), and vehicle control) via femoral vein with dosage of 8.4 mg/kg at 2 or 6 hours after MCA ligation for three consecutive days.

Neurological Behavioral Measurements

Behavioral assessments were measured on day 28 after stroke. These measurements include (a) body asymmetry and (b) locomotor activity (Shyu et al. 2004) and grip strength as previously described with modification (Shyu et al. 2004). The baseline-test scores were recorded in order to normalize those taken after cerebral ischemia. The elevated body swing test (EBST) was used to assess body asymmetry after MCA ligation and evaluated quantitatively as previously described (Shyu et al. 2004). Initially, animals were examined for lateral movement by suspending their bodies by their tails. The frequency of initial head swing contralateral to the ischemic side was counted in twenty continuous tests and was normalized, as follows: % recovery=[1−(lateral swings in twenty tests−10)/10 ×100%. Locomotor activity: Rats were subjected to VERSAMAX ANIMAL ACTIVITY™ monitoring (ACCUSCAN INSTRUMENTS™) for about 2 h for behavioral recording. The VERSAMAX ANIMAL ACTIVITY™ monitoring contained 16 horizontal and 8 vertical infrared sensors spaced 87 cm apart. The vertical sensors were situated 10 cm from the floor of the chamber. Motor activity was counted as the number of beams broken by a rat movement in the chamber. Three vertical parameters defined in the manufacturer's menu option were calculated over 2 h at night: (i) vertical activity, (ii) vertical time, and (iii) number of vertical movements. Grip strength was analyzed using GRIP STRENGTH METER™ (TSE SYSTEMS™); percentage of improvement in grip strength was measured on each forelimb separately and was calculated as the ratio between the mean strength out of 20 pulls of the side contralateral to the ischemia and the ipsilateral side (Shyu et al. 2004). In addition, the ratio of grip strength post-treatment and baseline were also calculated and changes were presented as a percentage of baseline value.

Measurement of Infarct Size Using Magnetic Resonance Image (MRI)

MRI was performed on rats under anesthesia in an imaging system (R4, GETM) at 3.0 T. Brains were scanned in 6 to 8 coronal image slices, each 2 mm thick without any gaps. T2-weighted imaging (T2WI) pulse sequences were obtained with the use of a spin-echo technique (repetition time, 4000 ms; echo time, 105 ms) and were captured sequentially for each animal at day 7 after cerebral ischemia. To measure the infarction area in the right cortex, we subtracted the noninfarcted area in the right cortex from the total cortical area of the left hemisphere (Shyu et al. 2004). The area of infarct was drawn manually from slice to slice, and the volume was then calculated by internal volume analysis software (VOXTOOL™, GENERAL ELECTRIC™).

[18F]Fluoro-2-deoxyglucose Positron Emission Tomography (FDG-PET) Examination

To assess the metabolic activity and synaptic density of brain tissue, experimental rats were examined using MICROPET™ scanning of [18F]fluoro-2-deoxyglucose (FDG) to measure relative metabolic activity under the protocol previously described (Matsumura et al. 2003). In brief, 18F was produced by the 18O(p, n)18F nuclear reaction in a cyclotron at China Medical University and Hospital, Taiwan, and 18F-FDG was synthesized as previously described (Hamacher et al. 1986) with an automated 18F-FDG synthesis system (NIHON KOKAN™). Data were collected with a high-resolution small-animal PET (MICROPET™, RODENT R4™, CONCORDE MICROSYSTEMS™) scanner. The system parameters have been described previously by Carmichael et al. (Carmichael et al. 2004). After one week of each treatment, animals anesthetized with chloral hydrate (0.4 g/kg, ip), fixed in a customized stereotactic head holder and positioned in the microPET scanner. Then the animals were given an intravenous bolus injection of 18F-FDG (200-250 µCi/rat) dissolved in 0.5 mL of saline. Data acquisition began at the same time and continued for 60 min using a 3-D acquisition protocol. The image data acquired from microPET were displayed and analyzed by INTERACTIVE DATA LANGUAGE™(IDL) ver. 5.5 (RESEARCH SYSTEMS™) and ASIPRO™ ver. 3.2 (CONCORDE MICROSYSTEMS™) software. FDG-PET images were reconstructed using a posterior-based 3-dimentional iterative algorithm (Kornblum et al. 2000) and overlaid on MR templates to confirm anatomical location (Brownell et al. 1998). Coronal sections for striatal and cortical measurements represented brain areas between 0 and +1 mm from bregma, and thalamic measurements represented brain areas between −2 and −3 mm from bregma, as estimated by visual inspection of the unlesioned side. The relative metabolic activity in regions of interest (ROI) of the striatum was expressed as a percentage deficit as previously described with modification (Carmichael et al. 2004).

Statistical Analysis

All measurements in this study were performed blindly. Results were expressed as mean +SEM. The behavioral scores have been evaluated for normality. Student's t-tests were used to evaluate mean differences between the vehicle-control and the treated group. Data lacking normal distribution were analyzed by a nonparametric ANOVA (Kruskal-Wallis test). A value of P<0.05 was taken as significant.

iPS Methods

Human iPS cells differentiated into NPCs in vitro (iPS-NPCs):

iPS-MEF-Ng-20D-17 from Kyoto University, and Cell Bank of RIKEN BioResource Center of Japan (Okita K. et al. Nature (2007) 448(7151):313-17) was induced into iPS-NPCs using a multistage differentiation protocol with some modifications (Kumagai G. et al. PLoS ONE (2009) 4(11): e7706). In brief, the human iPS cells expanding on irradiated MEF feeder cells were passaged, and then transferred to nonadherent culture dishes where they readily formed spheroid embryoid bodies (EBs). Clusters of neuroepithelial-like cells could be isolated and propagated from EBs in the medium of DMEM-F12, N2 supplement (1%; Invitrogen), and 20 ng/mL FGF-2 (R&D SYSTEMSTM™, Germany). These cells showed a typical neural progenitor cells (NPCs) morphology and homogeneously expressed the neural stem cell marker proteins GFAP (1:200, CHEMICON™), nestin (1:300, CHEMICON™), and Tuj-1 (1:500, CHEMICON™).

Intracerebral transplantation of iPS-NPCs.

Prior to transplantation, the iPS-NPSs were labeled using 1 µg/mL bis-benzimide (HOECHST™33342; SIGMA™) for 1 hours at 37° C. as previously described (Shyu WC. et al. J Clin Invest (2008) 118(1):133-148). Labeled cells were then collected and washed in PBS three times. iPS-NPCs were counted using a cytometer to ensure an adequate cell number for transplantation. One week after brain ischemia, adult male Sprague-Dawley rats (weight >300 g) were anesthetized with chloral hydrate (0.4 g/kg, ip) and injected stereotaxically with approximately 1 ×106 cells in a 3-5 μL PBS suspension through a 26-gauge Hamilton syringe into 3 cortical areas adjacent to the right MCA, 3.0 to 5.0 mm below the dura. The control animals were administered PBS only. The approximate coordinates for these sites were 1.0 to 2.0 mm anterior to the bregma and 3.5 to 4.0 mm lateral to the midline, 0.5 to 1.5 mm posterior to the bregma and 4.0 to 4.5 mm lateral to the midline, and 3.0 to 4.0 mm posterior to the bregma and 4.5 to 5.0 mm lateral to the midline. The needle was retained in place for 5 minutes after each injection and a piece of bone wax was applied to the skull defects to prevent leakage of the injected solution.

Peptide treatments:

After transplantation, intravenous PTENK13 (8.4 mg/kg) or saline through femoral vein once a day for 7 days was given to one of the iPS-NPC-implanted groups. Immunosuppressant of FK506 (2 μg/g i.p., PROGRAF™, FUJISAWA HEALTHCARE™) injections were given daily to each experimental rat from the day after cerebral ischemia.

ALS Mice Methods

Transgenic mice expressing G37R SOD1 (G37R) at almost 8 months of age and having no apparent pathologic symptoms were double blinded with a designated code and divided into 3 groups of 12 mice (6 male and 6 female) maintained on a pure C57BL6 background in the local animal facility under a 12 h light cycle with food and drinking water ad libitum. All mice were genotyped by PCR. The use of animals as described in this study was carried out according to The Guide to the Care and Use of Experimental Animals of the Canadian Council on Animal Care. Two peptides, the active PTEN peptide of K13 and the K mutated to R control peptide (K13K-R) were IP-injected 3 times a week with a dose of 16 mg/kg.

Body weight and neurological scores such as HLR scores and Rota Rod functions were regularly monitored and recorded. End points and survival dates were determined when mice were not able to stand up within 20 s when moved on the side. Disabled mice were anesthetized and sacrificed according to the guidelines of The University of British Columbia for the care and use of laboratory animals. All collected data were subjected to statistical analysis using Kaplan-Meier plots and Log-rank tests.

EXAMPLE 1

NMDAR Activation Enhances PTEN Nuclear Translocation

The results of both LDH assay and nuclei staining showed that the NMDA treatment (20 uM, 1 hour) caused significant cell death in cultured hippocampal neurons (FIG. 1a and 1b). NMDAR activation enhanced PTEN nuclear translocation in cultured neurons, determined by both immunostaining of endogenous PTEN, and western blotting of subcellular fractions. The purity of the different cellular fractions was confirmed by probing each fraction for corresponding subcellular marker proteins (FIG. 1c-e). The NMDA treatment reduced the level of nuclear PIP3, which is a substrate of nuclear PTEN (FIG. 1f). Two mutants of PTEN were over-expressed into cultured hippocampal neurons. One is the phosphatase dead mutant PTENC124S-GFP, and the other is wild-type PTEN-GFP, while both of them are fused with nuclear localization signal (NLS). A significantly lower death rate in the PTENC124S-GFP group (FIG. 1g and 1h) demonstrates that the phosphatase activity of nuclear PTEN is critical in NMDAR-mediated excitotoxicity.

EXAMPLE 2

Figure 2:
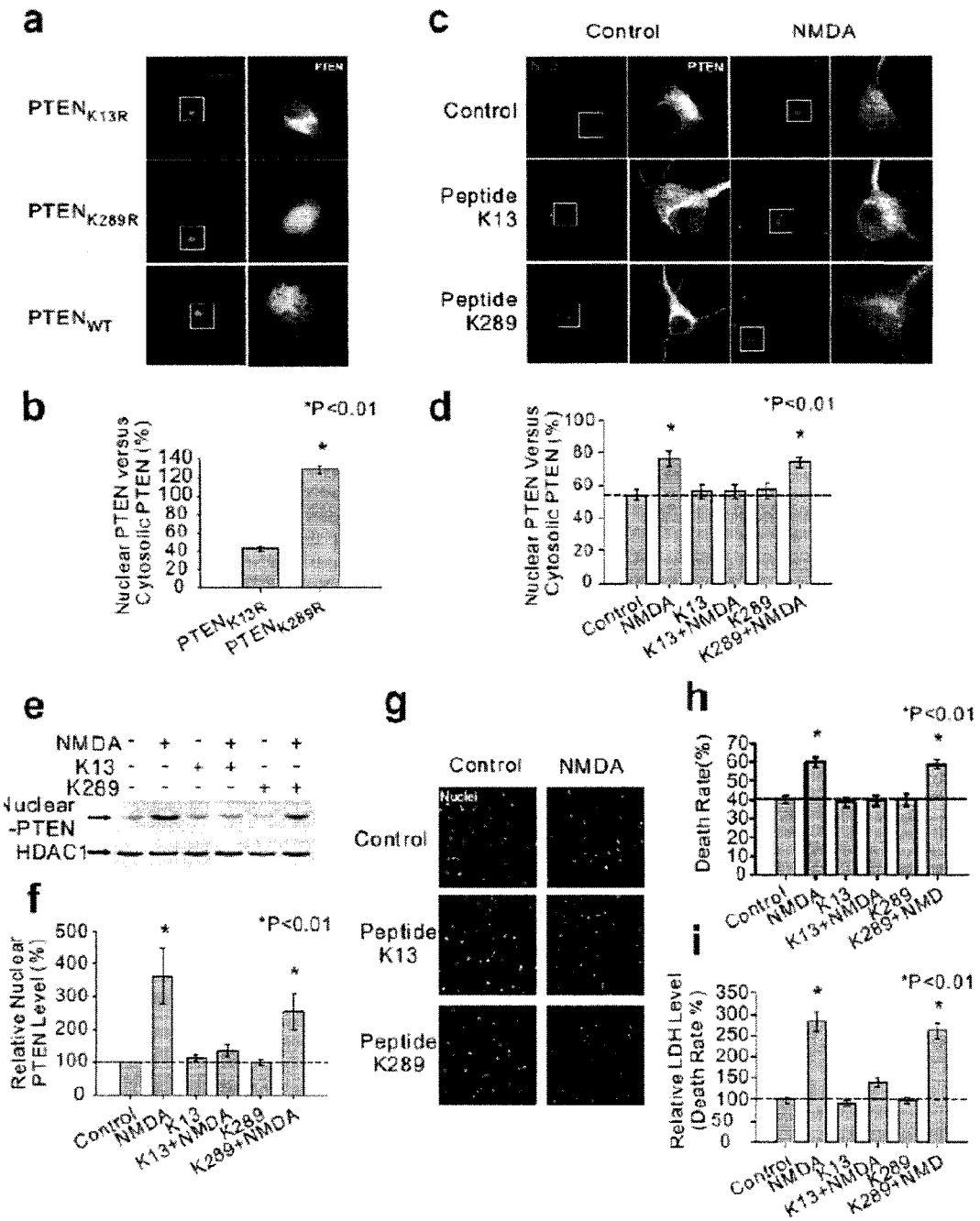
FIG. 2 shows blocking PTEN nuclear translocation with interfering Peptide-K13 rescues NMDAR-mediated excitotoxicity. (a, b) Two PTEN mutants, PTENK13R-GFP and PTENK289R-GFP, were constructed and transfected into cultured hippocampal neurons respectively. Nuclear versus cytoplasmic localization of each was measured (c, d) Two peptides that flank the K13 and K289 sites respectively were synthesized, with the Peptide-K289 functioning as a control for Peptide-K13. Nuclear versus cytoplasmic localization of each was measured, with or without stimulation by NMDA. (e, f). The western blotting result of nuclear fractions from cultured neurons treated with Peptide-K13 and Peptide-K289, with or without NMDA stimulation. (g, h, i). NMDAR-mediated cell death, determined by both (g, h) nuclei staining (Hoechst 33342) and (i) LDH assay (Sigma, #TOX7).

Blocking PTEN Nuclear Translocation with Interfering Peptide-K13 Rescues NMDAR-Mediated Excitotoxicity Previous research, based on studies in cell lines (PC3 and 298T), showed that two lysine resides, K13 and K289, are the major mono-ubiquitination sites on PTEN and essential for PTEN nuclear import. However, whether the neuronal PTEN adopts the same mechanism is unknown. Thus, two PTEN mutants, PTENK13R-GFP and PTENK289R-GFP, were constructed and transfected into cultured hippocampal neurons respectively. The result showed that PTENK13R-GFP mutant displayed a predominantly cytoplasmic localization, while both the PTENK289R-GFP mutant and widetype PTEN-GFP showed an even distribution between cytosolic and nuclear compartments. Therefore, we conclude that the K13 site, compared with K289 site, is likely more critical for PTEN nuclear translocation in neurons (FIGS. 2a and 2b). Two peptides that flank the K13 and K289 sites respectively were synthesized and fused to a TAT protein transduction domain, with the Peptide-K289 (SEQ ID NO: 4) functioning as a control for Peptide-K13 (SEQ ID NO: 1). The result of endogenous PTEN immunostaining showed that Peptide-K13 (10 uM), which blocks PTEN mono-ubiquitination, prevented PTEN nuclear translocation, while Peptide-K289 (10 uM) failed to do so (FIGS. 2c and 2d). The western blotting result of nuclear fractions from cultured neurons showed that Peptide-K13, which blocks PTEN mono-ubiquitination, prevents PTEN nuclear translocation, while Peptide-K289 failed to do so (FIGS. 2e and 2f). Peptide-K13, which blocks PTEN nuclear translocation, significantly prevents NMDAR-mediated cell death, determined by both nuclei staining and LDH assay (FIGS. 2g and 2h).

EXAMPLE 3

Figure 3:
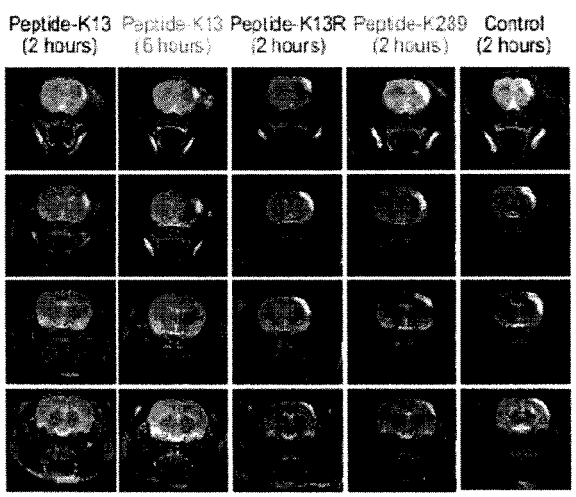
FIG. 3 shows administration of PTEN peptide reduces the infarct volume (MRI) and improves glucose metabolic activity (FDG-PET) after cerebral ischemia. In order to select the most effective treatment of PTEN peptide, Sprague-Dawley rats (~200 g) were assigned into 5 groups with different type of peptide treatment (i.v. 8.4 mg/kg) (1) Peptide-K13, given 2 hours after ischemia onset, (2) Peptide-K13, given 6 hours after ischemia onset, (3) Peptide-K13R, given 2 hours after ischemia onset, (4) Peptide-K289, given 2 hours after ischemia onset, and (5) Saline, given 2 hours after ischemia onset. Each group n=10. (a) At seven days after cerebral ischemia, infarct volume assessed by MRI. (b) Cortical glucose metabolism was examined by FDG-PET one week after treatment.
Figure 3:
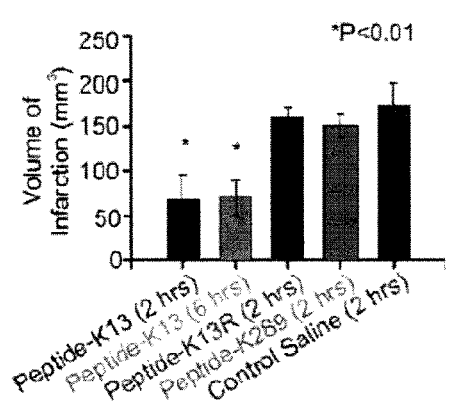
Figure 3:
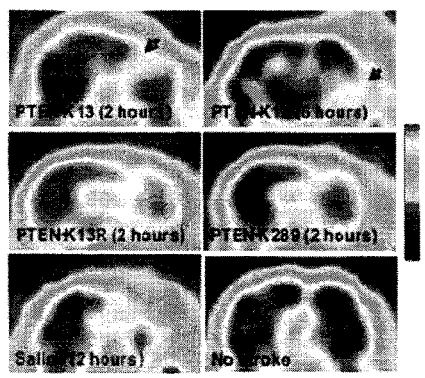
Figure 3:
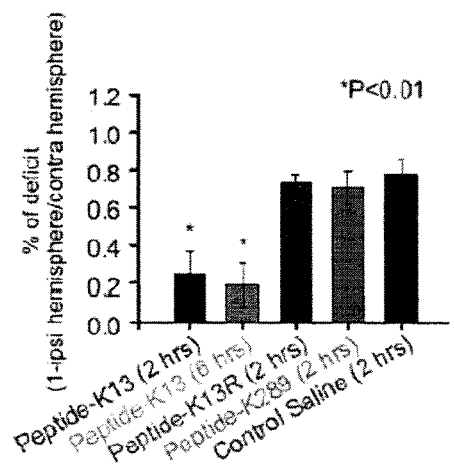

Administration of PTEN Peptide Reduces the Infarct Volume (MRI) and Improves Glucose Metabolic Activity (FDG-PET) After Cerebral Ischemia In order to select the most effective treatment of PTEN peptide, Sprague-Dawley rats (~200g) were assigned into 5 groups with different type of peptide treatment (i.v. 8.4 mg/kg) (1) Peptide-K13 (SEQ ID NO: 2), given 2 hours after ischemia onset, (2) Peptide-K13, given 6 hours after ischemia onset, (3) Peptide-K13R (SEQ ID NO: 3), given 2 hours after ischemia onset, (4) Peptide-K289 (SEQ ID NO: 4), given 2 hours after ischemia onset, and (5) Saline, given 2 hours after ischemia onset. Each group n=10. At seven days after cerebral ischemia (FIG. 3a), infarct volume assessed by MRI was significantly reduced in Peptide-K13-treated rats (2 hours and 6 hours group), compared with other groups. To verify whether intravenous PTEN peptide administration could enhance metabolic activity, cortical glucose metabolism was examined by FDG-PET one week after treatment. The microPET images (FIG. 3b) showed a striking increase in FDG uptake over the right cortex of the Peptide-K13-treated groups (2 hours and 6 hours), which was significantly better than in Peptide-K13R-, Peptide-K289- and Saline-treated rats.

EXAMPLE 4

Figure 4:
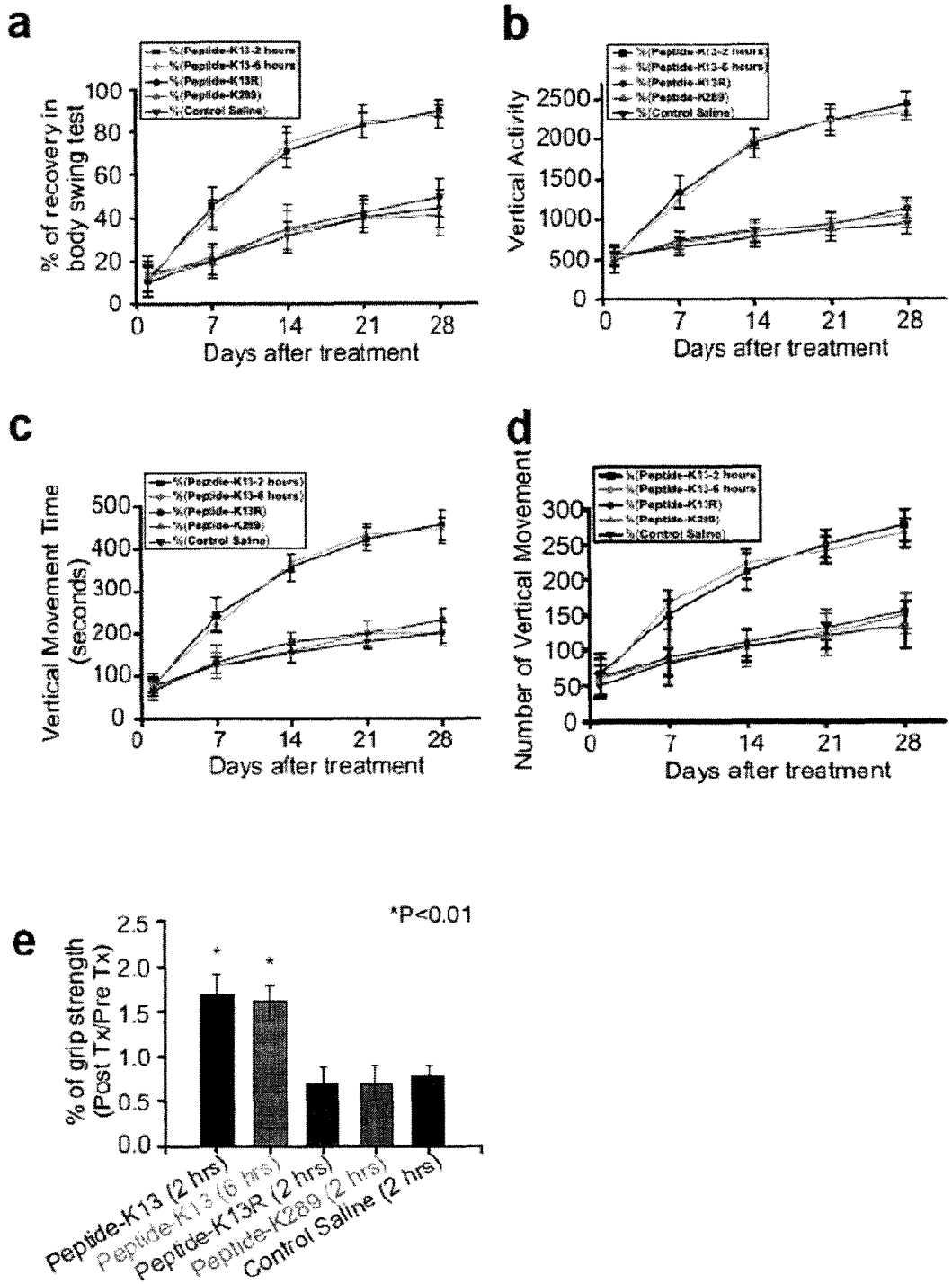
FIG. 4 shows intravenous injection of PTEN peptide improves motor behavioral performances after cerebral ischemia. Body asymmetry, locomotor activity tests and grip strength measurement were used to assess the neurological deficit recovery in Peptide-K13-(2 hours and 6 hours), Peptide-K13R-(2 hours), Peptide-K289-(2 hours) and saline-(2 hours) treated rats (n=10 per group). (a) Recovery in body swing tests than rats treated with Peptide-K13R, or Peptide-K289, or saline. (b, c, d) Locomotor activities (including measurement on vertical activity, vertical time, and number of vertical movements) in rats receiving Peptide-K13 treatment, Peptide-K289, or saline (2 hours and 6 hours). (e) A comparison of forelimb grip strength before and 28 days after ischemia for the Peptide-K13-treated group, Peptide-K289 group or saline group (2 hours and 6 hours).

Intravenous Injection of PTEN Interference Peptide Improves Motor Behavioral Performances After Cerebral Ischemia Body asymmetry, locomotor activity tests and grip strength measurement were used to assess the neurological deficit recovery in Peptide-K13-(2 hours and 6 hours), Peptide-K13R-(2 hours), Peptide-K289-(2 hours) and saline-(2 hours) treated rats (n=10 per group). Peptide-K13-treated rats (2 hours and 6 hours) showed much more recovery in body swing tests than rats treated with Peptide-K13R, or Peptide-K289, or saline (FIG. 4a). Locomotor activities (including measurement on vertical activity, vertical time, and number of vertical movements) were significantly better after cerebral ischemia in rats receiving Peptide-K13 treatment (2 hours and 6 hours) than other groups (FIG. 4b-d). In addition, in a comparison of forelimb grip strength before and 28 days after ischemia, the Peptide-K13-treated group (2 hours and 6 hours) had a much better strength ratio than all other groups (FIG. 4e).

EXAMPLE 5

PTEN Peptide Reduces the Infarct Volume in a Dose Dependent Manner

Figure 5:
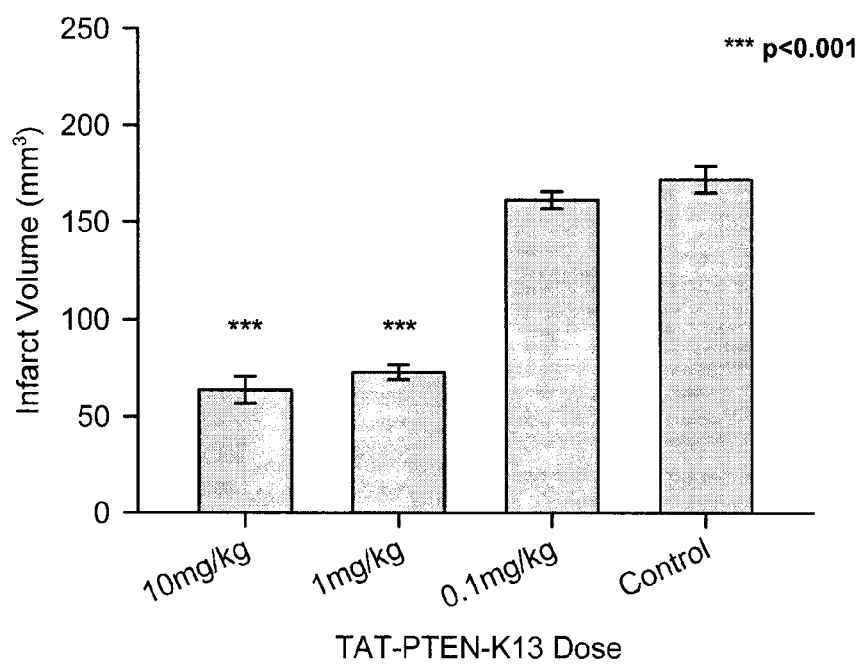
FIG. 5 shows administration of PTEN peptide reduces the infarct volume after cerebral ischemia. Treatment of Sprague-Dawley rats (~200 g) with PTEN peptideat 3 different doses (10 mg/kg; 1.0 mg/kg; and 0.1 mg/kg) as compared to saline control, where administration was 2 hours after ischemia onset and seven days after cerebral ischemia infarct volume was assessed by MRI.

Administration of TAT-PTEN-K13 (SEQ ID NO:2) at different intravenous doses was administered to four groups of Sprague-Dawley rats (~200 g—8 per group) (1) 10 mg/kg (2) 1.0 mg/kg (3) 0.1 mg/kg (4) Saline (control), given 6 hours after ischemia onset. FIG. 5 shows a greater than 50% decrease in infarct volume with 10 mg/kg and 1.0 mg/kg as compared to the control.

TABLE 3

| Group Name | n | Missing | Mean | Std Dev | SEM |
|---|---|---|---|---|---|
| PTEN (10 mg) | 8 | 0 | 63.700 | 19.445 | 6.875 |
| PTEN (1 mg) | 8 | 0 | 72.850 | 10.609 | 3.751 |
| PTEN (0.1 mg) | 8 | 0 | 160.900 | 11.911 | 4.211 |
| Control | 8 | 0 | 171.412 | 19.683 | 6.959 |

The differences in the mean values among the treatment groups are greater than would be expected by chance; there is a statistically significant difference (P=<0.001). Power of performed test with alpha=0.050: 1.000. All Pairwise Multiple Comparison Procedures (Holm-Sidak method): Overall significance level=0.05.

EXAMPLE 6

Figure 6:
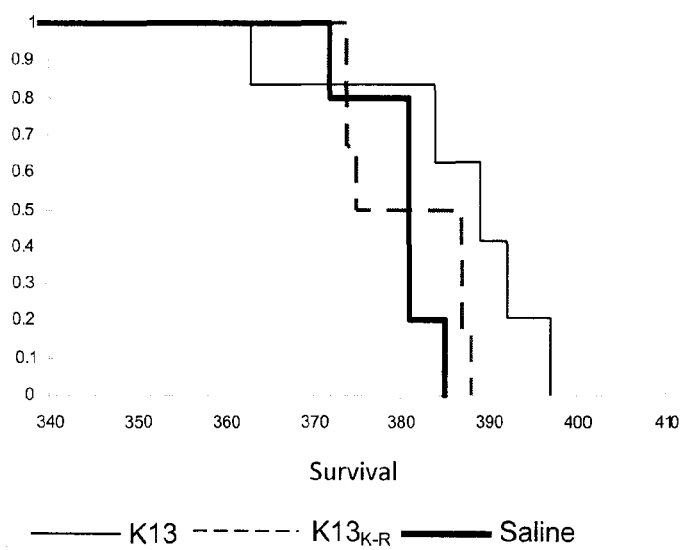
FIGS. 6A and 6B show Tat-K13 PTEN peptide administration in a transgenic mouse model of ALS for female and male mice respectively.
Figure 6:
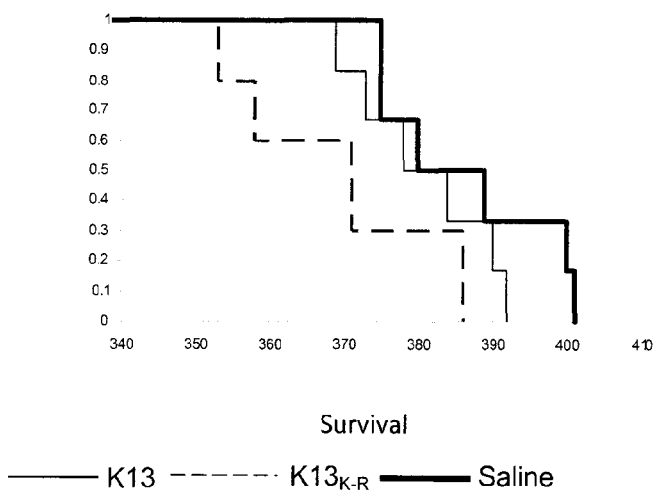

Tat-K13 PTEN Peptide Improves Gender Dependent Survival and Improves Behavioural Outcomes in a Transgenic Animal Model of ALS The Tat-K13 PTEN peptide prolongs the survival and improves behavioural outcomes of female ALS mice. FIG. 6A shows a statistically significant increase in female mice given Tat-K13 PTEN peptide as compared to the mutated Tat-K13$_{K-R}$ PTEN and saline controls. However, in the male mice no statistically significant improvement was seen with the Tat-K13 PTEN peptide (see FIG. 6B). Gender-specific effects are observed in many animal models of disease.

EXAMPLE 7

Tat-K13 Promotes the Survival of iPS-NPC Intracerebral Transplantated into the Infarction Areas After Focal Cerebral Ischemia in the Rat The isolated polypeptide Tat-K13 increases the survival of stem cells transplanted into the brain when given to the recipient animal prior to transplantation or incubated with the stem cell prior to their transplantation. One of the major challenges for clinical use of stem cell transplantation is the low survival rate of the transplanted cells.

Figure 7:
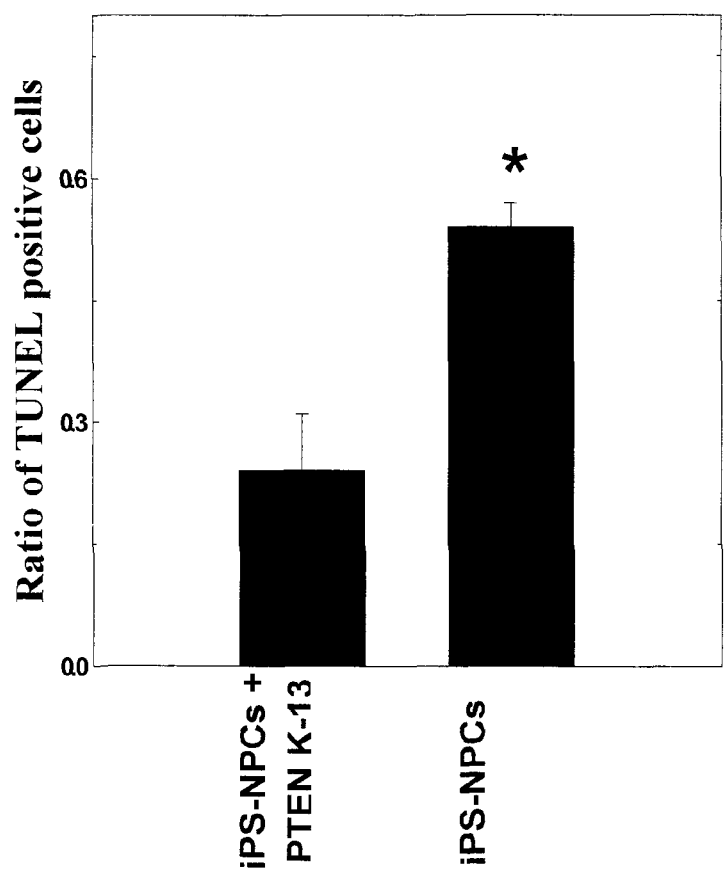
FIG. 7 shows immnoflourescent co-localization of apoptotic marker TUNEL performed at 7 days after transplantation demonstrated that Tat-K13-treated rats (iPS-NPCs+ PTENK13) contained significantly fewer TUNEL positive transplanted iPS-NPSc than that of saline-treated rats (iPS-NPCs).

Stem cell transplantation is considered an attractive cell replacement therapy to treat various neurodegenerative disorders. However, experimental results have demonstrated that only very small fraction of the transplanted stem cells could survive to engraft for 1 week after the transplantation (Gojo S, Exp Cell Res 2003; 288:51-9; Müller-Ehmsen J, J Mol Cell Cardiol (2006) 41:876-84). As demonstrated in FIG. 7, blocking PTEN nuclear translocation with systemic application of Tat-K13 following transplantation significantly increased the survival rate of transplanted human induced pluripotent stem cells-derived neural progenitor cells (iPS-NPCs) transplanted into the ischemic area of the rat subjected to stroke (focal cerebral ischemia produced by the unilateral ligation of MAO as described above). Immnoflourescent co-localization of apoptotic marker TUNEL performed at 7 days after transplantation demonstrated that Tat-K13-treated rats (iPS-NPCs+PTENK13) contained significantly fewer TUNEL positive transplanted iPS-NPSc than that of saline-treated rats (iPS-NPCs) (n=6 each group). These results strongly suggest that the PTENK13 has a stem cell survival promoting activity, thereby having important therapeutic applications for promoting stem cell replacement therapies in treating variety of neurodegenerative disorders, for example, ranging from stroke, Huntington's disease, ALS, Parkinson's disease and non-neuronal degenerative diseases.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings. Further, citation of references herein is not an admission that such references are prior art to the present invention nor does it constitute any admission as to the contents or date of these documents.

REFERENCES

Baker, S. J. (2007). "PTEN enters the nuclear age." Cell 128(1): 25-8.

Brownell, A. L., E. Livni, et al. (1998). "In vivo PET imaging in rat of dopamine terminals reveals functional neural transplants." Ann Neurol 43(3): 387-90.

Carmichael, S. T., K. Tatsukawa, et al. (2004). "Evolution of diaschisis in a focal stroke model." Stroke 35(3): 758-63.

Hamacher, K., H. H. Coenen, et al. (1986). "Efficient stereospecific synthesis of no-carrier-added 2-[18F]- fluoro-2-deoxy-D-glucose using aminopolyether supported nucleophilic substitution." *J Nucl Med* 27(2): 235-8.

Hudson, P. J. and C. Souriau (2003). "Engineered antibodies." *Nat Med* 9(1): 129-34.

Kornblum, H. I., D. M. Araujo, et al. (2000). "In vivo imaging of neuronal activation and plasticity in the rat brain by high resolution positron emission tomography (microPET)." *Nat Biotechnol* 18(6): 655-60.

Lecerf, J. M., T. L. Shirley, et al. (2001). "Human single-chain Fv intrabodies counteract in situ huntingtin aggregation in cellular models of Huntington's disease." *Proc Natl Acad Sci U S A* 98(8): 4764-9.

Li, J., C. Yen, et al. (1997). "PTEN, a putative protein tyrosine phosphatase gene mutated in human brain, breast, and prostate cancer." *Science* 275(5308): 1943-7.

Lian, Z. and A. Di Cristofano (2005). "Class reunion: PTEN joins the nuclear crew." *Oncogene* 24(50): 7394-400.

Matsumura, A., S. Mizokawa, et al. (2003). "Assessment of microPET performance in analyzing the rat brain under different types of anesthesia: comparison between quantitative data obtained with microPET and ex vivo autoradiography." *Neuroimage* 20(4): 2040-50.

Mielke, J, G. and Y. T. Wang (2005). "Insulin exerts neuroprotection by counteracting the decrease in cell-surface GABA receptors following oxygen-glucose deprivation in cultured cortical neurons." *J Neurochem* 92(1): 103-13.

Ning, K., L. Pei, et al. (2004). "Dual neuroprotective signaling mediated by downregulating two distinct phosphatase activities of PTEN." *J Neurosci* 24(16): 4052-60.

Shen, W. H., A. S. Balajee, et al. (2007). "Essential role for nuclear PTEN in maintaining chromosomal integrity." *Cell* 128(1): 157-70.

Shyu, W. C., S. Z. Lin, et al. (2005). "Overexpression of PrPC by adenovirus-mediated gene targeting reduces ischemic injury in a stroke rat model." *J Neurosci* 25(39): 8967-77.

Shyu, W. C., S. Z. Lin, et al. (2004). "Functional recovery of stroke rats induced by granulocyte colony-stimulating factor-stimulated stem cells." *Circulation* 110(13): 1847-54.

Steck, P. A., M. A. Pershouse, et al. (1997). "Identification of a candidate tumour suppressor gene, MMAC1, at chromosome 10q23.3 that is mutated in multiple advanced cancers." *Nat Genet* 15(4): 356-62.

Trotman, L. C., X. Wang, et al. (2007). "Ubiquitination regulates PTEN nuclear import and tumor suppression." *Cell* 128(1): 141-56.

Wang, X., Y. Shi, et al. (2008). "Crucial role of the C-terminus of PTEN in antagonizing NEDD4-1-mediated PTEN ubiquitination and degradation." *Biochem J* 414 (2): 221-9.

Wang, X., L. C. Trotman, et al. (2007). "NEDD4-1 is a proto-oncogenic ubiquitin ligase for PTEN." *Cell* 128(1): 129-39.

---

What is claimed is:

1. A method for treating cerebral ischemia comprising administering a biologically effective amount of a composition comprising a polypeptide conjugate comprising the amino acid sequence of SEQ ID NO: 2 to a subject in need thereof.

2. The method of claim 1, wherein said biologically effective amount is an amount sufficient to prevent cell death.

3. The method of claim 1, wherein the composition further comprises a carrier selected from the group consisting of a solid support; a stabilizer; a preservative; and a pharmaceutically acceptable carrier.

* * * * *

UNITED STATES PATENT AND TRADEMARK OFFICE
CERTIFICATE OF CORRECTION

PATENT NO. : 10,258,666 B2
APPLICATION NO. : 14/810223
DATED : April 16, 2019
INVENTOR(S) : Wang et al.

Page 1 of 1

It is certified that error appears in the above-identified patent and that said Letters Patent is hereby corrected as shown below:

In the Specification

At Column 1, Line 28:
Delete "PI3KJAKT" and replace it with --PI3K/AKT--.

At Column 19, Line 21:
Delete "NRI" and replace it with --NR1--.

Signed and Sealed this
Tenth Day of December, 2019

Andrei Iancu
*Director of the United States Patent and Trademark Office*

SEQUENCE LISTING

```
<160> NUMBER OF SEQ ID NOS: 7

<210> SEQ ID NO 1
<211> LENGTH: 14
<212> TYPE: PRT
<213> ORGANISM: Homo sapiens

<400> SEQUENCE: 1

Lys Glu Ile Val Ser Arg Asn Lys Arg Arg Tyr Gln Glu Asp
1               5                   10

<210> SEQ ID NO 2
<211> LENGTH: 25
<212> TYPE: PRT
<213> ORGANISM: Artificial Sequence
<220> FEATURE:
<223> OTHER INFORMATION: PTEN K13 interference peptide conjugated to TAT
      protein transduction domain
<220> FEATURE:
<221> NAME/KEY: MISC_FEATURE
<222> LOCATION: (1)..(14)
<223> OTHER INFORMATION: PTEN K13 interference peptide
<220> FEATURE:
<221> NAME/KEY: MISC_FEATURE
<222> LOCATION: (15)..(25)
<223> OTHER INFORMATION: TAT protein transduction domain

<400> SEQUENCE: 2

Lys Glu Ile Val Ser Arg Asn Lys Arg Arg Tyr Gln Glu Asp Tyr Gly
1               5                   10                  15

Arg Lys Lys Arg Arg Gln Arg Arg Arg
            20                  25

<210> SEQ ID NO 3
<211> LENGTH: 25
<212> TYPE: PRT
<213> ORGANISM: Artificial Sequence
<220> FEATURE:
<223> OTHER INFORMATION: PTEN K13 interference peptide conjugated to TAT
``` protein transduction domain with modified K13 ubiquitination site
<220> FEATURE:
<221> NAME/KEY: MISC_FEATURE
<222> LOCATION: (1)..(14)
<223> OTHER INFORMATION: PTEN K13R interference peptide
<220> FEATURE:
<221> NAME/KEY: MISC_FEATURE
<222> LOCATION: (8)..(8)
<223> OTHER INFORMATION: K13 ubiquitination site modified to an arginine
    (R) residue
<220> FEATURE:
<221> NAME/KEY: MISC_FEATURE
<222> LOCATION: (15)..(25)
<223> OTHER INFORMATION: TAT protein transduction domain

<400> SEQUENCE: 3

Lys Glu Ile Val Ser Arg Asn Arg Arg Arg Tyr Gln Glu Asp Tyr Gly
1               5                   10                  15

Arg Lys Lys Arg Arg Gln Arg Arg Arg
            20                  25

<210> SEQ ID NO 4
<211> LENGTH: 23
<212> TYPE: PRT
<213> ORGANISM: Artificial Sequence
<220> FEATURE:
<223> OTHER INFORMATION: PTEN K289 interference peptide conjugated to TAT
    protein transduction domain
<220> FEATURE:
<221> NAME/KEY: MISC_FEATURE
<222> LOCATION: (1)..(11)
<223> OTHER INFORMATION: TAT protein transduction domain
<220> FEATURE:
<221> NAME/KEY: MISC_FEATURE
<222> LOCATION: (12)..(23)
<223> OTHER INFORMATION: PTEN K289 interference peptide

<400> SEQUENCE: 4

Tyr Gly Arg Lys Lys Arg Arg Gln Arg Arg Arg Pro Glu Glu Thr Ser
1               5                   10                  15

Glu Lys Val Glu Asn Gly Ser
            20

<210> SEQ ID NO 5
<211> LENGTH: 14
<212> TYPE: PRT
<213> ORGANISM: Homo sapiens

<400> SEQUENCE: 5

Lys Glu Ile Val Ser Arg Asn Lys Arg Tyr Gln Glu Asp
1               5                   10

<210> SEQ ID NO 6
<211> LENGTH: 14
<212> TYPE: PRT
<213> ORGANISM: Homo sapiens

<400> SEQUENCE: 6

Lys Glu Ile Val Ser Arg Asn Lys Arg Tyr Gln Glu Asp
1               5                   10

<210> SEQ ID NO 7
<211> LENGTH: 403
<212> TYPE: PRT
<213> ORGANISM: Homo sapiens

<400> SEQUENCE: 7

Met Thr Ala Ile Ile Lys Glu Ile Val Ser Arg Asn Lys Arg Arg Tyr

```
1               5                    10                   15
Gln Glu Asp Gly Phe Asp Leu Asp Leu Thr Tyr Ile Tyr Pro Asn Ile
                20                   25                   30
Ile Ala Met Gly Phe Pro Ala Glu Arg Leu Glu Gly Val Tyr Arg Asn
                35                   40                   45
Asn Ile Asp Asp Val Val Arg Phe Leu Asp Ser Lys His Lys Asn His
 50                       55                   60
Tyr Lys Ile Tyr Asn Leu Cys Ala Glu Arg His Tyr Asp Thr Ala Lys
 65                  70                  75                   80
Phe Asn Cys Arg Val Ala Gln Tyr Pro Phe Glu Asp His Asn Pro Pro
                85                   90                   95
Gln Leu Glu Leu Ile Lys Pro Phe Cys Glu Asp Leu Asp Gln Trp Leu
                100                  105                  110
Ser Glu Asp Asp Asn His Val Ala Ala Ile His Cys Lys Ala Gly Lys
                115                  120                  125
Gly Arg Thr Gly Val Met Ile Cys Ala Tyr Leu Leu His Arg Gly Lys
                130                  135                  140
Phe Leu Lys Ala Gln Glu Ala Leu Asp Phe Tyr Gly Glu Val Arg Thr
145                  150                  155                  160
Arg Asp Lys Lys Gly Val Thr Ile Pro Ser Gln Arg Arg Tyr Val Tyr
                165                  170                  175
Tyr Tyr Ser Tyr Leu Leu Lys Asn His Leu Asp Tyr Arg Pro Val Ala
                180                  185                  190
Leu Leu Phe His Lys Met Met Phe Glu Thr Ile Pro Met Phe Ser Gly
                195                  200                  205
Gly Thr Cys Asn Pro Gln Phe Val Val Cys Gln Leu Lys Val Lys Ile
                210                  215                  220
Tyr Ser Ser Asn Ser Gly Pro Thr Arg Arg Glu Asp Lys Phe Met Tyr
225                  230                  235                  240
Phe Glu Phe Pro Gln Pro Leu Pro Val Cys Gly Asp Ile Lys Val Glu
                245                  250                  255
Phe Phe His Lys Gln Asn Lys Met Leu Lys Lys Asp Lys Met Phe His
                260                  265                  270
Phe Trp Val Asn Thr Phe Phe Ile Pro Gly Pro Glu Glu Thr Ser Glu
                275                  280                  285
Lys Val Glu Asn Gly Ser Leu Cys Asp Gln Glu Ile Asp Ser Ile Cys
                290                  295                  300
Ser Ile Glu Arg Ala Asp Asn Asp Lys Glu Tyr Leu Val Leu Thr Leu
305                  310                  315                  320
Thr Lys Asn Asp Leu Asp Lys Ala Asn Lys Asp Lys Ala Asn Arg Tyr
                325                  330                  335
Phe Ser Pro Asn Phe Lys Val Lys Leu Tyr Phe Thr Lys Thr Val Glu
                340                  345                  350
Glu Pro Ser Asn Pro Glu Ala Ser Ser Thr Ser Val Thr Pro Asp
                355                  360                  365
Val Ser Asp Asn Glu Pro Asp His Tyr Arg Tyr Ser Asp Thr Thr Asp
                370                  375                  380
Ser Asp Pro Glu Asn Glu Pro Phe Asp Glu Asp Gln His Thr Gln Ile
385                  390                  395                  400
Thr Lys Val
```